United States Patent [19]

Hashimoto et al.

[11] Patent Number: 5,254,578
[45] Date of Patent: Oct. 19, 1993

[54] BENZOPYRAN DERIVATIVES HAVING ANTI-HYPERTENSIVE AND VASODILATORY ACTIVITY AND THEIR THERAPEUTIC USE

[75] Inventors: Toshihiko Hashimoto; Hidekazu Masuko; Hiroyuki Koike; Toshio Sada, all of Tokyo, Japan

[73] Assignee: Sankyo Company, Limited, Tokyo, Japan

[21] Appl. No.: 973,560

[22] Filed: Nov. 9, 1992

Related U.S. Application Data

[63] Continuation of Ser. No. 778,527, Oct. 18, 1991, abandoned.

[30] Foreign Application Priority Data

Oct. 24, 1990 [JP] Japan .................................. 2-286617

[51] Int. Cl.$^5$ .................... A61K 31/40; C07D 405/04
[52] U.S. Cl. .................................. 514/414; 548/454
[58] Field of Search ............... 514/337, 414; 546/269; 548/454

[56] References Cited

U.S. PATENT DOCUMENTS

| | | | |
|---|---|---|---|
| 4,616,021 | 10/1986 | Ashwood et al. | 514/309 |
| 4,908,378 | 3/1990 | Soll et al. | 514/414 |
| 4,925,839 | 6/1988 | Quagliato et al. | 514/212 |

FOREIGN PATENT DOCUMENTS

| | | |
|---|---|---|
| 0273262 | 12/1987 | European Pat. Off. |
| 0314446 | 10/1988 | European Pat. Off. |
| 0350805 | 7/1989 | European Pat. Off. |
| 0413438 | 2/1991 | European Pat. Off. |
| 3923839 | 1/1991 | Fed. Rep. of Germany |

OTHER PUBLICATIONS

Janssens et al, "Synthetic 1,4-Disubstituted-1,4-dihydro-5H-tetrazol-5-one Derivatives of Fentanyl: Alfentanil (R 39209), a Potent, Extremely Short-Acting Narcotic Analgesic"; J. Med. Chem., 29, 2290-2297 (1986).

Primary Examiner—Joseph P. Brust
Assistant Examiner—Jacqueline Haley
Attorney, Agent, or Firm—Frishauf, Holtz, Goodman & Woodward

[57] ABSTRACT

Compounds of the formula:

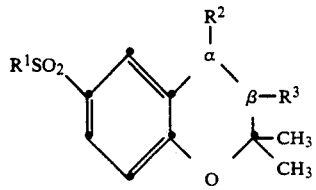

in which:
$R^1$ is a trifluoromethyl or a pentafluoroethyl;
$R^2$ is

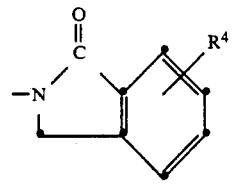

in which $R^4$ is hydrogen;
α-β is a carbon-carbon single bond;

and pharmaceutically acceptable salts thereof, have antihypertensive activity and can thus be used for the treatment and prophylaxis of cardiovascular diseases.

9 Claims, No Drawings

BENZOPYRAN DERIVATIVES HAVING ANTI-HYPERTENSIVE AND VASODILATORY ACTIVITY AND THEIR THERAPEUTIC USE

This application is a continuation of application Ser. No. 778,527, filed Oct. 18, 1991, now abandoned.

BACKGROUND TO THE INVENTION

The present invention relates to a series of new benzopyran derivatives which have an anti-hypertensive activity and can thus be used for the treatment and prophylaxis of cardiovascular diseases. The invention also provides methods and compositions using these compounds as well as processes for their preparation.

The compounds of the present invention are the 3,4-dihydro-2,2-dimethyl-4-(1-oxoisoindolin-2-yl)-6-perfluoroalkylsulfonyl-2H-1-benzopyran-3-ol compounds, the 3,4-dihydro-4-(1,2-dihydro-2-oxo-1-pyridyl)-2,2-dimethyl-6-trifluoromethylsulfonyl-2H-1-benzopyran-3-ol compounds, nitrates of these compounds, analogs of these compounds having a carbon-carbon unsaturated bond at the 3,4-position of the pyran ring and derivatives of these compounds and their nitrates in which the isoindolinyl or pyridyl ring is substituted.

Certain compounds of this type and having this type of activity are disclosed in J. Med. Chem., 29, 2194 (1986), in European Patent Specifications No. 350 805, 273 262 and 314 446 (equivalent to U.S. Pat. No. 4,925,839), and in U.S. Pat. No. 4,908,378, and, of the compounds disclosed in the prior art references referred to here, the closest to the compounds of the present invention are disclosed in European Patent Specification No. 350 805 and U.S. Pat. No. 4,908,378 and are believed to be 6-cyano-3,4-dihydro-2,2-dimethyl-4-(2-oxo-1-pyrrolidinyl)-2H-1.benzopyran-3-ol (which has the formula A given below), 3,4-dihydro-2,2-dimethyl-6-trifluoromethylsulfonyl-4-(2-oxo-1-pyrrolidinyl)-2H-1-benzopyran-3-ol (which has the formula B given below) and 3,4-dihydro-2,2-dimethyl-4-(1-oxoisoindolin-2-yl)-6-trifluoromethylsulfonyl-2H-1-benzopyran-3-ol (which has the formula C given below):

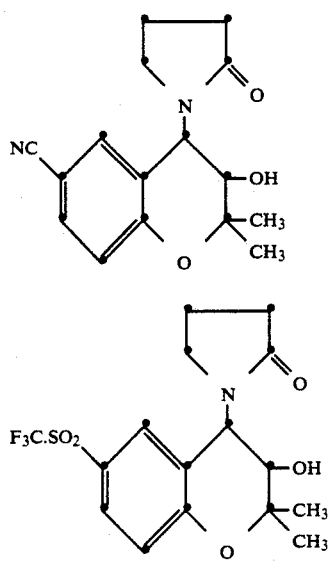

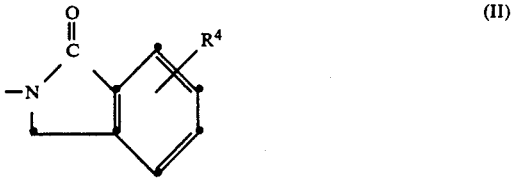

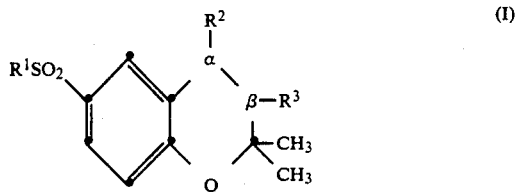

The [(+)-6-cyano-3,4-dihydro-2,2-dimethyl trans-4-(2-oxo-1-pyrrolidinyl)-2H-1-benzopyran-3-ol isomer of Compound A, known as Cromakalim, is believed to be under investigation as a possible commercial vasodilating agent.

Although these prior compounds have acceptable and useful activities, their activities and, especially, duration of action are less than is considered desirable.

We have now surprisingly discovered a limited series of compounds which have a similar class of activity and which have a combination of a 1-oxoisoindolin-2-yl or 1,2-dihydro-2-oxo-1-pyridyl group at the 4.position and a perfluoroalkylsulfonyl group at the 6-position, and which, as a result, are more potent and have a longer duration of action.

BRIEF SUMMARY OF INVENTION

It is, therefore, an object of the present invention to provide a series of new benzopyran derivatives which have vasodilatory and anti-hypertensive activities.

It is a further object of the invention to provide such compounds which have improved activities.

Other objects and advantages of the invention will become apparent as the description proceeds.

The compounds of the present invention are those compounds of formula (I):

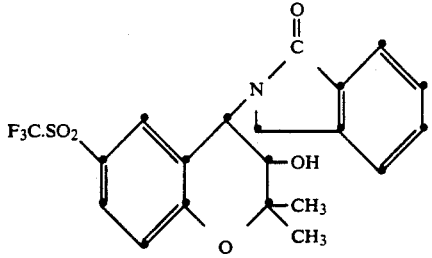

in which:

$R^1$ represents a perfluoroalkyl group having from 1 to 3 carbon atoms;

$R^2$ represents a group of formula (II):

(II)

in which $R^4$ represents a hydrogen atom, an alkyl group having from 1 to 4 carbon atoms, an alkoxy group having from 1 to 4 carbon atoms, a halogen atom, a trifluoromethyl group, a cyano group, a hydroxy group or a nitro group;

or a group of formula (III):

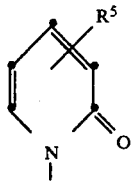 (III)

in which R⁵ represents a hydrogen atom, an alkyl group having from 1 to 4 carbon atoms, an alkoxy group having from 1 to 4 carbon atoms, a halogen atom, a trifluoromethyl group, a cyano group or a nitro group;

$\alpha$-$\beta$ represents a carbon-carbon single bond (CH-CH) or a carbon-carbon double bond (C=C); and where $\alpha$-$\beta$ represents a carbon-carbon single bond, R³ represents a hydroxy group or a nitrooxy group (—O—NO₂) or, where $\alpha$-$\beta$ represents a carbon-carbon double bond, R³ represents a hydrogen atom;

and pharmaceutically acceptable salts thereof;

PROVIDED THAT R¹ does not represent a trifluoromethyl group when R² represents a group of formula (II), $\alpha$-$\beta$ represents a single bond, R³ represents a hydroxy group and R⁴ represents a hydrogen atom.

The invention also provides a composition for the treatment or prophylaxis of cardiovascular disease, which comprises an effective amount of at least one active compound in admixture with a carrier or diluent, wherein the active compound is at least one compound of formula (I) or a pharmaceutically acceptable salt thereof.

The invention still further provides a method of treating hypertension and cardiac malfunctions which comprises administering to an animal, preferably a mammal, which may be human, at least one active compound, wherein the active compound is at least one compound of formula (I) or a pharmaceutically acceptable salt thereof.

The invention also provides processes for preparing the compounds of the present invention which are described in greater detail hereafter.

DETAILED DESCRIPTION OF INVENTION

In the compounds of formula (I), where R¹ represents a perfluoroalkyl group, the alkyl part has from 1 to 3 carbon atoms and may be a straight or branched chain group, although it is preferably a straight chain group; such groups are the trifluoromethyl, pentafluoroethyl, heptafluoropropyl and heptafluoroisopropyl groups, of which the trifluoromethyl and pentafluoroethyl groups are preferred and the trifluoromethyl group is more preferred.

R² may represent said group of formula (II) or (III), of which the group of formula (II) is preferred.

Where R⁴ or R⁵ represents an alkyl group, this may be a straight or branched chain alkyl group having from 1 to 4 carbon atoms, and examples include the methyl, ethyl, propyl, isopropyl, butyl, isobutyl, sec-butyl and t-butyl groups, preferably a methyl, ethyl, propyl, isopropyl or butyl group, and most preferably the methyl group.

Where R⁴ or R⁵ represents an alkoxy group, this may be a straight or branched chain alkoxy group having from 1 to 4 carbon atoms, and examples include the methoxy, ethoxy, propoxy, isopropoxy, butoxy, isobutoxy, sec-butoxy and t-butoxy groups, preferably a methoxy, ethoxy, propoxy, isopropoxy or butoxy group, and most preferably the methoxy group.

Where R⁴ or R⁵ represents a halogen atom, this may be, for example, a fluorine, chlorine, bromine or iodine atom, preferably a fluorine or chlorine atom, and more preferably a fluorine atom.

Preferably R⁴ represents a hydrogen atom, a methyl group, a methoxy group, a halogen atom (of which the fluorine and chlorine atoms are preferred), a trifluoromethyl group, a cyano group or a nitro group, more preferably a fluorine atom, a chlorine atom or a nitro group, and most preferably a fluorine atom.

Preferably R⁵ represents a hydrogen atom, a methyl group, a methoxy group, a halogen atom (of which the fluorine and chlorine atoms are preferred), a trifluoromethyl group, a cyano group or a nitro group, more preferably a hydrogen atom, a fluorine atom, a chlorine atom or a nitro group and most preferably a hydrogen atom.

Where R² represents a group of formula (II), we prefer that $\alpha$-$\beta$ should represent a carbon-carbon single bond, and thus that R³ should represent a hydroxy group or a nitrooxy group; in this case, we also prefer that the oxoisoindolinyl group should be substituted, i.e. R⁴ should not represent a hydrogen atom. Where R² represents a group of formula (III), we prefer that $\alpha$-$\beta$ should represent a carbon-carbon double bond, In the compounds of formula (I), where R² represents a group of formula (II) and R⁴ represents a hydroxy group, the compound is acidic, and it can therefore form a salt. There is no particular restriction on the nature of these salts, provided that, where they are intended for therapeutic use, they should be pharmaceutically acceptable. Where they are intended for non-therapeutic uses, e.g. as intermediates in the preparation of other, and possibly more active, compounds, even this restriction does not apply. Examples of such salts include: salts with an alkali metal, such as sodium, potassium or lithium; salts with an alkaline earth metal, such as barium or calcium; salts with another metal, such as magnesium or aluminum; organic base salts, such as a salt with dicyclohexylamine; and salts with a basic amino acid, such as lysine or arginine.

Where $\alpha$-$\beta$ represents a carbon-carbon single bond, the compounds of the present invention can form various stereoisomers and optical isomers. Although all of these stereoisomers and optical isomers, including racemates, are represented herein by a single general formula (I), the present invention envisages both the individual isomers and mixtures thereof. Preferred compounds are those containing the 3,4-trans configuration, particularly those containing the (3S,4R) configuration. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Preferred classes of compounds of the present invention are those compounds of formula (I) in which:

(1) R¹ represents a trifluoromethyl group or a pentafluoroethyl group;

(2) R² represents:

a group of formula (II), in which R⁴ represents a hydrogen atom, a methyl group, a methoxy group, a halogen atom (of which the fluorine and chlorine atoms are preferred), a trifluoromethyl group, a cyano group or a nitro group, and more preferably a chlorine atom, a fluorine atom or a nitro group, and most preferably a fluorine atom or a nitro group;

or a group of formula (III), in which $R^5$ represents a hydrogen atom, a methyl group, a methoxy group, a halogen atom (of which the fluorine and chlorine atoms are preferred), a trifluoromethyl group, a cyano group or a nitro group, more preferably a hydrogen atom, a fluorine atom, a chlorine atom or a nitro group and most preferably a hydrogen atom.

and particularly those in which $R^1$ is as defined in (1) above and $R^2$ is as defined in (2) above.

The more preferred compounds of the present invention are those compounds of formula (I) in which:

(3) $R^2$ represents a group of formula (II), in which $R^4$ represents a hydrogen atom, and either:

α-β represents a carbon-carbon single bond and $R^3$ represents a nitrooxy group, or α-β represents a carbon-carbon double bond and $R^3$ represents a hydrogen atom;

(4) $R^2$ represents a group of formula (II), in which $R^4$ represents a fluorine atom, a chlorine atom or a nitro group, and either:

α-β represents a carbon-carbon single bond and $R^3$ represents a hydroxy group or a nitrooxy group, or α-β represents a carbon-carbon double bond and $R^3$ represents a hydrogen atom; or (5) $R^2$ represents a group of formula (III), in which $R^5$ represents a hydrogen atom, α-β represents a carbon-carbon single bond and $R^3$ represents a nitrooxy group;

and particularly those in which $R^1$ is as defined in (1) above and $R^2$, $R^3$ and α-β are as defined in (3), (4) or (5) above.

Still more preferred compounds of the present invention are those compounds of formula (I) in which:

(6) $R^1$ represents a trifluoromethyl group;

and particularly those in which $R^1$ is as defined in (6) above and $R^2$, $R^3$ and α-β are as defined in (4) above.

The most preferred compounds of the present invention are those compounds of formula (I) in which:

(7) $R^2$ represents a group of formula (II), in which $R^4$ represents a fluorine atom, α-β represents a carbon-carbon single bond, and $R^3$ represents a hydroxy group;

and particularly those in which $R^1$ is as defined in (6) above and $R^2$, $R^3$ and α-β are as defined in (7) above.

Examples of certain of the compounds of the present invention are shown by the following formulae (I-1) and (I-2), in which the symbols used in the formulae are as defined in the respective one of Tables 1 and 2, that is Table 1 relates to formula (I-1) and Table 2 relates to formula (I-2).

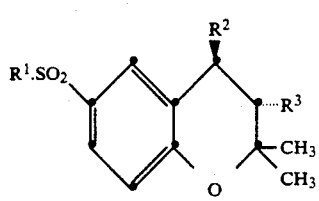
(I-1)

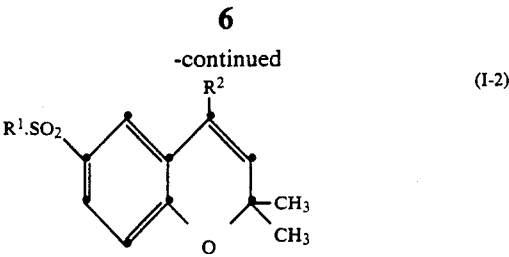
(I-2)

TABLE 1

| Compound No. | $R^1$ | $R^2$ | $R^3$ |
|---|---|---|---|
| 1-1 | $(CF_3)_2CF-$ | 1-oxoisoindolin-2-yl | OH |
| 1-2 | $CF_3CF_2-$ | 1-oxoisoindolin-2-yl | OH |
| 1-3 | $CF_3CF_2CF_2-$ | 1-oxoisoindolin-2-yl | OH |
| 1-4 | $CF_3CF_2CF_2-$ | 1,2-dihydro-2-oxo-1-pyridyl | OH |
| 1-5 | $CF_3$ | 1-oxoisoindolin-2-yl | $ONO_2$ |
| 1-6 | $CF_3CF_2-$ | 1-oxoisoindolin-2-yl | $ONO_2$ |
| 1-7 | $CF_3CF_2CF_2-$ | 1-oxoisoindolin-2-yl | $ONO_2$ |
| 1-8 | $CF_3CF_2CF_2-$ | 1,2-dihydro-2-oxo-1-pyridyl | $ONO_2$ |
| 1-9 | $CF_3$ | 6-fluoro-1-oxoisoindolin-2-yl | OH |
| 1-10 | $CF_3$ | 5-fluoro-1-oxoisoindolin-2-yl | OH |
| 1-11 | $CF_3$ | 6-chloro-1-oxoisoindolin-2-yl | OH |
| 1-12 | $CF_3$ | 5-chloro-1-oxoisoindolin-2-yl | OH |
| 1-13 | $CF_3$ | 4-nitro-1-oxoisoindolin-2-yl | OH |
| 1-14 | $CF_3$ | 7-nitro-1-oxoisoindolin-2-yl | OH |
| 1-15 | $CF_3$ | 6-nitro-1-oxoisoindolin-2-yl | OH |
| 1-16 | $CF_3$ | 4-fluoro-1-oxoisoindolin-2-yl | OH |
| 1-17 | $CF_3CF_2CF_2-$ | 3-methyl-1,2-dihydro-2-oxo-1-pyridyl | OH |
| 1-18 | $CF_3CF_2CF_2-$ | 3-methoxy-1,2-dihydro-2-oxo-1-pyridyl | OH |
| 1-19 | $CF_3CF_2CF_2-$ | 5-chloro-1,2-dihydro-2-oxo-1-pyridyl | OH |
| 1-20 | $CF_3CF_2-$ | 6-fluoro-1-oxoisoindolin-2-yl | OH |
| 1-21 | $CF_3CF_2-$ | 4-nitro-1-oxoisoindolin-2-yl | OH |
| 1-22 | $CF_3CF_2-$ | 6-nitro-1-oxoisoindolin-2-yl | OH |
| 1-23 | $CF_3CF_2-$ | 4-fluoro-1-oxoisoindolin-2-yl | OH |
| 1-24 | $CF_3$ | 1,2-dihydro-2-oxo-1-pyridyl | OH |
| 1-25 | $CF_3CF_2-$ | 1,2-dihydro-2-oxo-1-pyridyl | OH |
| 1-26 | $CF_3$ | 1,2-dihydro-2-oxo-1-pyridyl | $ONO_2$ |
| 1-27 | $CF_3CF_2-$ | 1,2-dihydro-2-oxo-1-pyridyl | $ONO_2$ |
| 1-28 | $CF_3$ | 6-methyl-1-oxoisoindolin-2-yl | OH |
| 1-29 | $CF_3$ | 4-methyl-1-oxoisoindolin-2-yl | OH |
| 1-30 | $CF_3$ | 6-methoxy-1-oxoisoindolin-2-yl | OH |
| 1-31 | $CF_3$ | 4-methoxy-1-oxoisoindolin-2-yl | OH |
| 1-32 | $CF_3$ | 6-cyano-1-oxoisoindolin-2-yl | OH |
| 1-33 | $CF_3$ | 4-cyano-1-oxoisoindolin-2-yl | OH |
| 1-34 | $CF_3CF_2-$ | 6-cyano-1-oxoisoindolin-2-yl | OH |
| 1-35 | $CF_3CF_2-$ | 4-cyano-1-oxoisoindolin-2-yl | OH |
| 1-36 | $CF_3$ | 6-fluoro-1-oxoisoindolin-2-yl | OH |
| 1-37 | $CF_3$ | 4-nitro-1-oxoisoindolin-2-yl | $ONO_2$ |
| 1-38 | $CF_3$ | 7-nitro-1-oxoisoindolin-2-yl | $ONO_2$ |
| 1-39 | $CF_3$ | 6-nitro-1-oxoisoindolin-2-yl | $ONO_2$ |
| 1-40 | $CF_3$ | 4-fluoro-1-oxoisoindolin-2-yl | $ONO_2$ |
| 1-41 | $CF_3$ | 3-methyl-1,2-dihydro-2-oxo-1-pyridyl | OH |
| 1-42 | $CF_3$ | 3-methoxy-1,2-dihydro-2-oxo-1-pyridyl | OH |
| 1-43 | $CF_3$ | 5-chloro-1,2-dihydro-2-oxo-1-pyridyl | OH |
| 1-44 | $(CF_3)_2CF-$ | 1-oxoisoindolin-2-yl | OH |
| 1-45 | $(CF_3)_2CF-$ | 1-oxoisoindolin-2-yl | $ONO_2$ |

TABLE 1-continued

| Compound No. | R¹ | R² | R³ |
|---|---|---|---|
| 1-46 | (CF$_3$)$_2$CF— | 1,2-dihydro-2-oxo-1-pyridyl | OH |
| 1-47 | (CF$_3$)$_2$CF— | 1,2-dihydro-2-oxo-1-pyridyl | ONO$_2$ |

TABLE 2

| Compound No. | R¹ | R² |
|---|---|---|
| 2-1 | CF$_3$ | 1-oxoisoindolin-2-yl |
| 2-2 | CF$_3$CF$_2$— | 1-oxoisoindolin-2-yl |
| 2-3 | CF$_3$CF$_2$CF$_2$— | 1-oxoisoindolin-2-yl |
| 2-4 | CF$_3$CF$_2$CF$_2$— | 1,2-dihydro-2-oxo-1-pyridyl |
| 2-5 | CF$_3$ | 6-fluoro-1-oxoisoindolin-2-yl |
| 2-6 | CF$_3$ | 5-fluoro-1-oxoisoindolin-2-yl |
| 2-7 | CF$_3$ | 6-chloro-1-oxoisoindolin-2-yl |
| 2-8 | CF$_3$ | 5-chloro-1-oxoisoindolin-2-yl |
| 2-9 | CF$_3$ | 4-fluoro-1-oxoisoindolin-2-yl |
| 2-10 | CF$_3$ | 4-nitro-1-oxoisoindolin-2-yl |
| 2-11 | CF$_3$ | 1,2-dihydro-2-oxo-1-pyridyl |
| 2-12 | CF$_3$ | 6-nitro-1-oxoisoindolin-2-yl |
| 2-13 | CF$_3$CF$_2$— | 6-fluoro-1-oxoisoindolin-2-yl |
| 2-14 | CF$_3$CF$_2$— | 5-fluoro-1-oxoisoindolin-2-yl |
| 2-15 | CF$_3$CF$_2$— | 6-chloro-1-oxoisoindolin-2-yl |
| 2-16 | CF$_3$CF$_2$— | 5-chloro-1-oxoisoindolin-2-yl |
| 2-17 | CF$_3$CF$_2$— | 4-fluoro-1-oxoisoindolin-2-yl |
| 2-18 | CF$_3$CF$_2$— | 4-nitro-1-oxoisoindolin-2-yl |
| 2-19 | CF$_3$CF$_2$— | 1,2-dihydro-2-oxo-1-pyridyl |
| 2-20 | CF$_3$CF$_2$— | 6-nitro-1-oxoisoindolin-2-yl |
| 2-21 | CF$_3$ | 4-fluoro-1,2-dihydro-2-oxo-1-pyridyl |
| 2-22 | CF$_3$ | 1,2-dihydro-4-nitro-2-oxo-1-pyridyl |
| 2-23 | CF$_3$ | 6-fluoro-1,2-dihydro-2-oxo-1-pyridyl |
| 2-24 | CF$_3$ | 1,2-dihydro-6-nitro-2-oxo-1-pyridyl |
| 2-25 | (CF$_3$)$_2$CF— | 1-oxoisoindolin-2-yl |
| 2-26 | (CF$_3$)$_2$CF— | 1,2-dihydro-2-oxo-1-pyridyl |

Of the compounds listed above, the following are preferred, that is to say Compounds No.: 1-2, 1-5, 1-6, 1-9, 1-13, 1-15, 1-16, 1-20, 1-21, 1-22, 1-23, 2-1, 2-2 and 2-19. The most preferred compounds are Compounds No.:

1-5. 3,4-Dihydro-2,2-dimethyl-4-(1-oxoisoindolin 2-yl)-6-trifluoromethylsulfonyl-2H-1-benzopyran-3-yl nitrate;

1-9. 3,4-Dihydro-2,2-dimethyl-4-(6-fluoro-1.oxoisoindolin-2-yl)-6-trifluoromethylsulfonyl-2H-1-benzopyran-3-ol;

1-13. 3,4-Dihydro 2,2-dimethyl-4-(4-nitro-1-oxoisoindolin-2-yl)-6-trifluoromethylsulfonyl-2H-1-benzopyran-3-ol;

1-15. 3,4-Dihydro-2,2-dimethyl-4-(6-nitro-1-oxoisoindolin-2-yl)-6-trifluoromethylsulfonyl-2H 1-benzopyran-3-ol;

1-16. 3,4-Dihydro-2,2-dimethyl-4-(4-fluoro-1-oxoisoindolin-2-yl)-6-trifluoromethylsulfonyl-2H-1-benzopyran-3-ol; and 2-1. 2,2-Dimethyl-4-(1-oxoisoindolin-2-yl)-6-trifluoromethylsulfonyl-2H-1-benzopyran;

and pharmaceutically acceptable salts thereof.

The compounds of the present invention may be prepared by a variety of methods well known for the preparation of compounds of this type. For example, they may be prepared by reacting a compound of formula (IV):

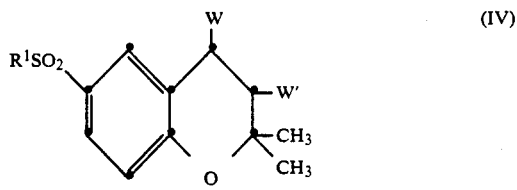

[in which R¹ is as defined above and either (a) W represents an amino group and W' represents a hydroxy group;

or (b) W and W' together represent an oxygen atom to form an epoxy group];

with, in case (a), a compound of formula (V):

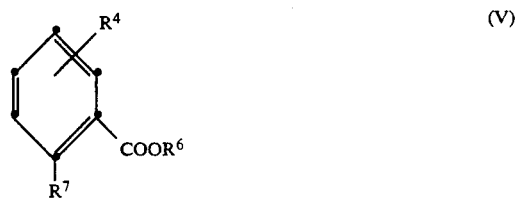

(in which R⁴ is as defined above, R⁶ represents an alkyl group having from 1 to 4 carbon atoms, and R⁷ represents a formyl group or a halomethyl group, preferably a bromomethyl, chloromethyl or iodomethyl group) or, in case (b), with a compound of formula (VI) or (VI'):

(in which R⁴ and R⁵ are as defined above and

represents a group of formula

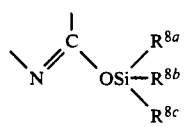

or

-continued

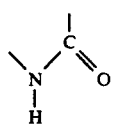

in which $R^{8a}$, $R^{8b}$ and $R^{8c}$ are the same or different and each represents an alkyl group having from 1 to 4 carbon atoms);

to give a compound of formula (Ia):

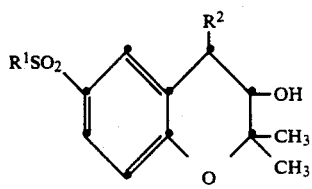

in which $R^1$ and $R^2$ are as defined above.

If desired, the compound of formula (Ia) can then be treated with a base to give a compound of formula (Ib):

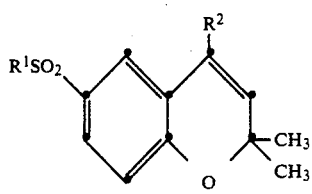

in which $R^1$ and $R^2$ are as defined above.

Alternatively, the compound of formula (Ia) can be reacted with a nitrating agent, to give a compound of formula (Ic):

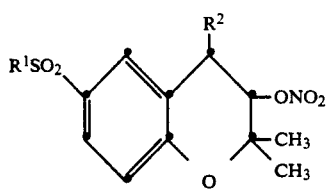

If desired, the product can then be salified, by conventional means.

In more detail, the compounds of the present invention can be prepared as illustrated in the following Reaction Schemes A and B.

Reaction Scheme A illustrates the preparation of a compound of formula (I) in which $R^2$ represents a group of formula (II), α-β represents a single bond and $R^3$ represents a hydroxy group, that is a compound of formula (Id), and the corresponding compound in which α-β represents a double bond, that is a compound of formula (Ie).

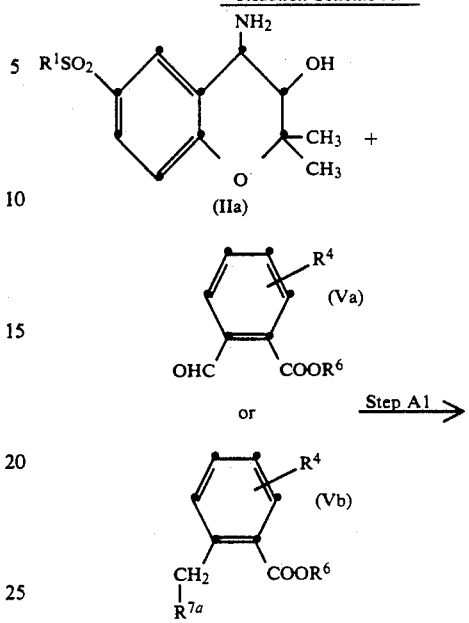

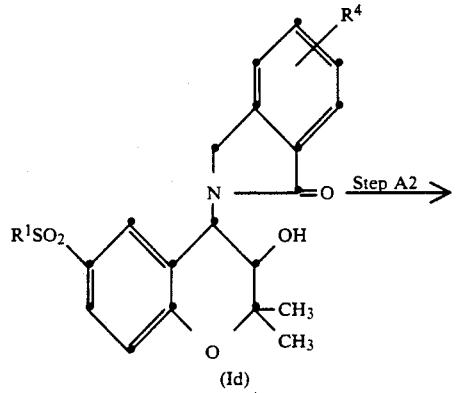

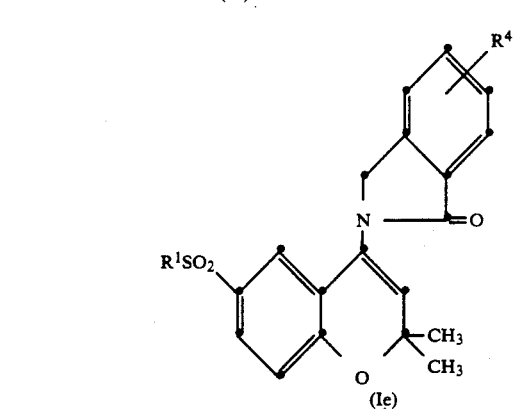

In the above formulae, $R^1$, $R^4$ and $R^6$ are as defined above, and $R^{7a}$ represents a halogen atom, preferably a bromine, chlorine or iodine atom.

In Step A1 of this Reaction Scheme, an aminoalcohol compound of formula (IIa) is reacted either with a formyl ester of formula (Va) or with a halo ester of formula (Vb), to give the compound of formula (Id).

The reaction of the aminoalcohol compound of formula (IIa) with the formyl ester of formula (Va) is normally and preferably effected in an inert solvent; it is also preferably effected in the presence of a reducing agent.

There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol or propanol; carboxylic acids, such as acetic acid or propionic acid; esters, such as ethyl acetate; ketones, such as acetone or methyl ethyl ketone; water; and mixtures of any two or more these solvents; of these, the alcohols, particularly methanol and propanol, are preferred, and propanol is most preferred.

Examples of reducing agents which may be used in this reaction include: borohydrides and cyanoborohydrides, such as sodium cyanoborohydride, sodium borohydride, zinc cyanoborohydride and zinc borohydride, of which sodium cyanoborohydride and zinc cyanoborohydride are most preferred. If required, the zinc compounds can be prepared from the corresponding sodium compounds and a zinc salt, for example zinc cyanoborohydride can be prepared from sodium cyanoborohydride and zinc chloride, in the course of the reaction.

The reaction can take place over a wide range of temperatures, and the precise reaction temperature is not critical to the invention. In general, we find it convenient to carry out the reaction at a temperature of from 0° C. to 150° C., more preferably from room temperature to 100° C. The time required for the reaction may also vary widely, depending on many factors, notably the reaction temperature and the nature of the reagents. However, provided that the reaction is effected under the preferred conditions outlined above, a period of from 1 hour to 72 hours, more preferably from 1 hour to 36 hours, will usually suffice.

Alternatively, the aminoalcohol compound of formula (IIa) may be reacted in Step A1 with a halo ester compound of formula (Vb). This reaction is preferably carried out in an inert solvent and also preferably in the presence of a base.

Examples of bases which may be used for this reaction include: alkali metal carbonates, such as potassium carbonate, sodium carbonate or lithium carbonate; alkali metal hydrogencarbonates, such as sodium hydrogencarbonate or potassium hydrogencarbonate; alkali metal hydrides, such as sodium hydride; alkali metal hydroxides, such as potassium hydroxide; and tertiary amines, such as triethylamine or diisopropylethylamine. Of these, we prefer the tertiary amines, the alkali metal carbonates and the alkali metal hydrogencarbonates.

There is no particular restriction on the nature of the solvent to be employed, provided that it has no adverse effect on the reaction or on the reagents involved and that it can dissolve the reagents, at least to some extent. Examples of suitable solvents include: nitriles, such as acetonitrile; aromatic hydrocarbons, such as benzene, toluene or xylene; ethers, such as diethyl ether, tetrahydrofuran or dioxane; halogenated hydrocarbons, especially halogenated aliphatic hydrocarbons, such as methylene chloride or dichloroethane; and amides, such as dimethylformamide or dimethylacetamide; of these, the nitriles and amides are preferred.

The reaction can take place over a wide range of temperatures, and the precise reaction temperature is not critical to the invention. In general, we find it convenient to carry out the reaction at a temperature of from 0° C. to 200° C., more preferably from room temperature to 170° C. The time required for the reaction may also vary widely, depending on many factors, notably the reaction temperature and the nature of the reagents. However, provided that the reaction is effected under the preferred conditions outlined above, a period of from 1 hour to 48 hours, more preferably from 1 hour to 10 hours, will usually suffice.

After completion of the reaction, the desired compound of the invention can be recovered from the reaction mixture by conventional means. For example, in one suitable recovery sequence, the reaction mixture is freed from the solvent by distillation, or poured into water and extracted with a water-immiscible organic solvent. The extract is then dried and the solvent is removed by distillation. Finally, if necessary, the desired compound can be further purified by conventional means, for example, by recrystallization or by the various chromatography techniques, notably column chromatography.

In Step A2 of Reaction Scheme A, a compound of formula (I) in which the bond of formula $\alpha$-$\beta$ is a double bond and $R^3$ represents a hydrogen atom, that is a compound of formula (Ie), can be prepared by treating the alcohol compound of formula (Id) with a base in the presence of an inert solvent.

Examples of bases which may be used in this reaction include: alkali metal hydroxides, such as sodium hydroxide or potassium hydroxide; soda talc (Merck Cat. No. 1567); and alkali metal hydrides, such as sodium hydride or potassium hydride; of these soda talc is preferred.

There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, dioxane or tetrahydrofuran; sulfoxides, such as dimethyl sulfoxide; and amides, especially fatty acid amides, such as dimethylformamide or dimethylacetamide; of these, the ethers are preferred.

The reaction can take place over a wide range of temperatures, and the precise reaction temperature is not critical to the invention. In general, we find it convenient to carry out the reaction at a temperature of from about room temperature to 180° C., more preferably from 50° C. to 150° C. The time required for the reaction may also vary widely, depending on many factors, notably the reaction temperature and the nature of the reagents. However, provided that the reaction is effected under the preferred conditions outlined above, a period of from 5 minutes to 2 hours, more preferably from 10 minutes to 1 hour will usually suffice.

After completion of the reaction, the desired compound of the invention can be recovered from the reaction mixture by conventional means. For example, in one suitable recovery procedure, the reaction mixture is freed from the solvent by distillation, or poured into water and extracted with a water-immiscible organic solvent. The extract is then dried, and the solvent is removed by distillation. Finally, if necessary, the desired compound can be further purified by conventional means, for example, by recrystallization or by the various chromatography techniques, notably column chromatography.

In Reaction Scheme B, we show how to prepare a compound of formula (I) in which $R^2$ represents a group of formula (III), the bond represented by $\alpha$-$\beta$ is a carbon-carbon single bond and $R^3$ represents a hydroxy group, that is a compound of formula (If), or a compound of formula (I) in which $R^2$ represents a group of formula (III) and the bond represented by $\alpha$-$\beta$ is a carbon-carbon double bond and $R^3$ represents a hydrogen atom, that is a compound of formula (Ig).

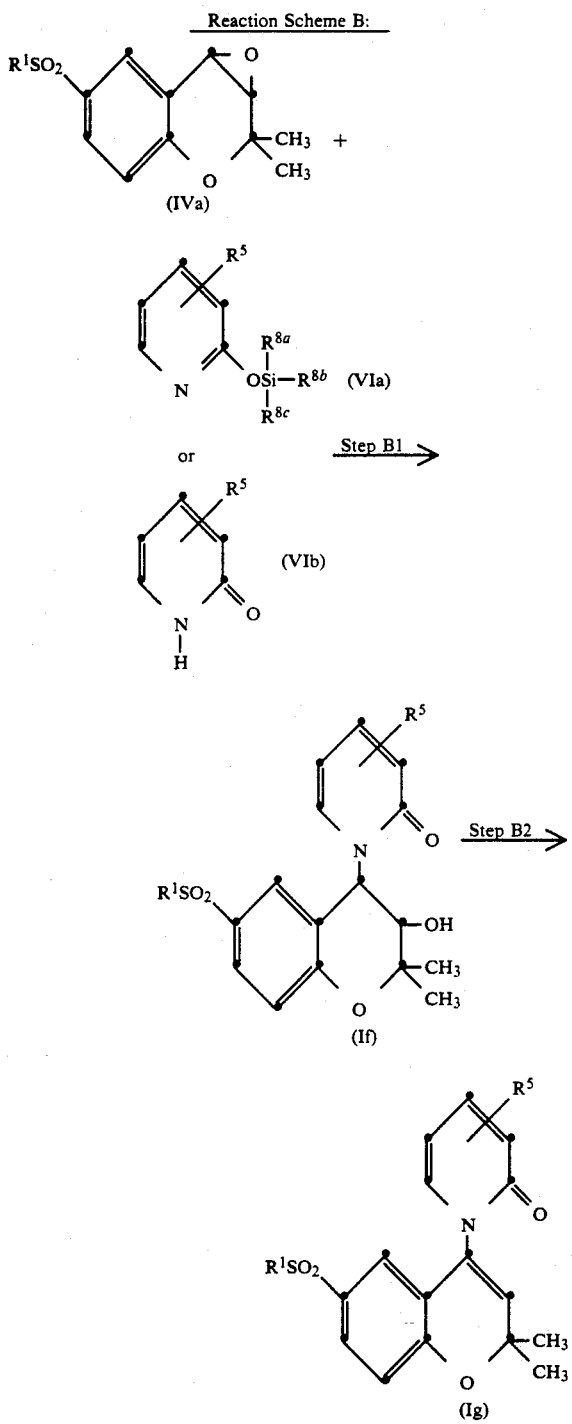

In Step B1 of Reaction Scheme B, the compound of formula (If) can be prepared by reacting an epoxy compound of formula (IVa) with a silyl ether compound of formula (VIa) or with a pyridone compound of formula (VIb).

The reaction of the compound of formula (IVa) with the silyl ether compound of formula (VIa) is preferably effected in the presence of a desilylating agent and also preferably in an inert solvent.

Examples of desilylating agents which may be used for this reaction include tetrabutylammonium fluoride and boron trifluoride, of which we prefer tetrabutylammonium fluoride.

There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxane; and hydrocarbons, particularly aromatic hydrocarbons, such as benzene, toluene or xylene, and aliphatic hydrocarbons, such as hexane or pentane; of these, the ethers are preferred.

The reaction can take place over a wide range of temperatures, and the precise reaction temperature is not critical to the invention. In general, we find it convenient to carry out the reaction at a temperature of from 0° C. to 50° C. (preferably at about room temperature). The time required for the reaction may also vary widely, depending on many factors, notably the reaction temperature and the nature of the reagents. However, provided that the reaction is effected under the preferred conditions outlined above, a period of from 10 hours to 96 hours (more preferably from 12 hours to 80 hours) will usually suffice.

The reaction of the compound of formula (IVa) with the pyridone compound of formula (VIb) is preferably carried out in an inert solvent in the presence of a base.

There is no particular restriction on the nature of the base employed in this reaction, and examples of bases which may be used include: amines, such as pyridine, triethylamine or 4-dimethylaminopyridine; alkali metal hydrides, such as sodium hydride or potassium hydride; alkali metal alkoxides, such as sodium methoxide, sodium ethoxide, potassium ethoxide or potassium t-butoxide; quaternary ammonium hydroxides, such as benzyltrimethylammonium hydroxide, tetrabutylammonium hydroxide or tetraethylammonium hydroxide; and alkali metal carbonates, such as potassium carbonate, sodium carbonate or lithium carbonate; of these, we prefer the alkali metal hydrides (particularly sodium hydride), the quaternary ammonium hydroxides (particularly benzyltrimethylammonium hydroxide) and the amines (particularly pyridine).

There is no particular restriction on the nature of the solvent to be employed, provided that it has no adverse effect on the reaction or on the reagents involved and that it can dissolve the reagents, at least to some extent. Where an alkali metal hydride is used in the reaction as the base, examples of suitable solvents include: ethers, such as diethyl ether, tetrahydrofuran or dioxane; amides, especially fatty acid amides, such as dimethylformamide or dimethylacetamide; and sulfoxides, such as dimethyl sulfoxide. Where alkali metal alkoxides, amines or quaternary ammonium hydroxides are used in the reaction as the base, we prefer to use alcohols, such as methanol, ethanol or propanol, as the solvent. Where carbonates are used for the reaction as the base, we prefer to use ketones (such as acetone or methyl ethyl ketone) or alcohols (such as methanol or ethanol) as the solvent. In particular, where an alkali metal hydride is used as the base, we most prefer to use an amide (particularly dimethylformamide) or a sulfoxide (particularly dimethyl sulfoxide) as the solvent; and, where the other bases are used for the reaction, we most prefer to use an alcohol (particularly methanol or ethanol) as the solvent.

The reaction can take place over a wide range of temperatures, and the precise reaction temperature is not critical to the invention. In general, we find it convenient to carry out the reaction at a temperature of from 0° C. to 150° C. (more preferably from 0° C. to 50° C.). The time required for the reaction may also vary widely, depending on many factors, notably the reaction temperature and the nature of the reagents. However, provided that the reaction is effected under the preferred conditions outlined above, a period of from 30 minutes to 48 hours (more preferably from 1 hour to 30 hours) will usually suffice.

After completion of the reaction, the desired compound of the invention can be recovered from the reaction mixture by conventional means. For example, in one suitable recovery sequence, the reaction mixture is freed from the solvent by distillation, or poured into water and extracted with a water-immiscible organic solvent. The extract is then dried and the solvent was removed by distillation. Finally, if necessary, the desired compound can be further purified by conventional means, for example, by recrystallization or by the various chromatography techniques, notably column chromatography.

In Step B2 of Reaction Scheme B, those compounds of formula (I) in which $R^3$ represents a hydrogen atom and the bond represented by $\alpha$-$\beta$ is a carbon-carbon double bond, that is, compounds of formula (Ig), can be prepared, if desired. This reaction is essentially the same as that described in Step A2 of Reaction Scheme A, and may be carried out using the same reagents and under the same conditions.

A compound of formula (Id) or (Ie) (see Reaction Scheme A) may also be prepared by the procedure described above in Reaction Scheme B, but replacing the pyridyl compound of formula (VIa) or (VIb) by a corresponding isoindoline compound of formula (VIc) or (VId):

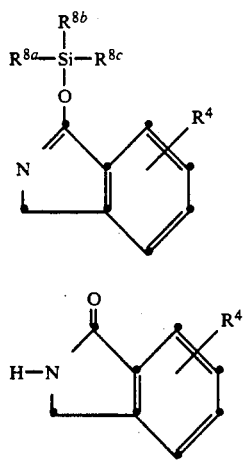

in which $R^4$, $R^{8a}$, and $R^{8c}$ are as defined above.

Compounds of formula (I) in which the bond represented by $\alpha$-$\beta$ is a carbon-carbon single bond and $R^3$ represents a nitrooxy (—$ONO_2$) group, that is to say compounds of formula (Ih):

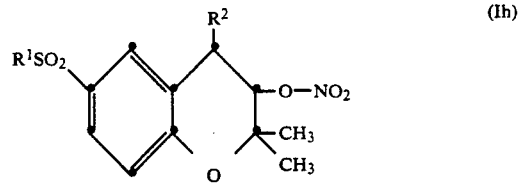

(in which $R^1$ and $R^2$ are as defined above) can be prepared by reacting the corresponding compound of formula (I) in which $R^3$ represents a hydroxy group [and which may have been prepared as described in either of Reaction Schemes A and B, e.g. a compound of formula (Id) or (If)] with a nitrating agent.

The reaction with the nitrating agent is normally and preferably carried out in the presence of an inert solvent.

There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, especially halogenated aliphatic hydrocarbons, such as methylene chloride, dichloroethane, carbon tetrachloride or chloroform; ethers, such as diethyl ether, dimethoxyethane or tetrahydrofuran; and hydrocarbons, especially aliphatic hydrocarbons, such as hexane or heptane. Of these, we prefer the halogenated aliphatic hydrocarbons.

Examples of nitrating agents which may be used for this reaction include: nitronium salts, such as nitronium tetrafluoroborate ($NO_2BF_4$), nitronium hexafluorophosphate ($NO_2PF_6$) or nitronium trifluoromethanesulfonate ($NO_2CF_3SO_3$); and nitric acid itself. Of these, we prefer the nitronium salts.

The reaction can take place over a wide range of temperatures, and the precise reaction temperature is not critical to the invention. In general, we find it convenient to carry out the reaction at a temperature of from 0° C. to 100° C., more preferably from 10° C. to 50° C. The time required for the reaction may also vary widely, depending on many factors, notably the reaction temperature and the nature of the reagents. However, provided that the reaction is effected under the preferred conditions outlined above, a period of from 10 minutes to 10 hours, more preferably from 20 minutes to 3 hours, will usually suffice.

After completion of the reaction, the desired compound of the invention can be recovered from the reaction mixture by conventional means. For example, in one suitable recovery technique the reaction mixture is freed from the solvent by distillation, or it is poured into water and extracted with a water-immiscible organic solvent. The extract is then dried, and the solvent was removed by distillation. Finally, if necessary, the resulting residue can be further purified by conventional means, for example, by recrystallization or by the various chromatography techniques, notably column chromatography.

In the compounds of formula (I), where the bond represented by $\alpha$-$\beta$ is a carbon-carbon single bond, the compound may form optically active isomers. In this case, an optically active isomer may be prepared by using an optically active compound of formula (IIa). The optically active compound of formula (IIa) can be prepared from the racemate by conventional means, for example, by treating the racemate of compounds of formula (II) with an optically active carboxylic acid [for example, (+) or (−)-tartaric acid, (+)- or (−)-dibenzoyltartaric acid, (−)-malic acid or (−)-mandelic acid] or with an optically active sulfonic acid (for example, camphorsulfonic acid) followed by recrystallizing the resulting salts.

If desired, a pharmaceutically acceptable salt of the compound of formula (I) can be prepared by treating the free acidic compound with a suitable base, for example an alkali metal hydroxide (such as sodium hydroxide or potassium hydroxide) or an organic amine (such as triethylamine or pyridine) in the presence of an inert solvent (for example, dioxane, tetrahydrofuran or diethyl ether) in a suitable solvent, and then distilling off the solvent.

The starting materials of formulae (IIa) and (IVa) used in Reaction Schemes A and B can easily be prepared by conventional means, for example as illustrated in the following Reaction Schemes D, E and F.

Reaction Scheme D:

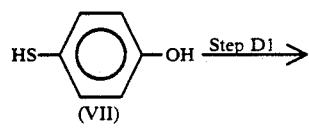

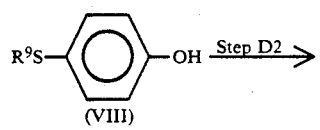

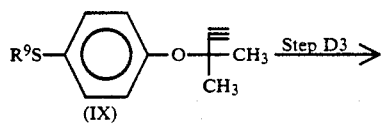

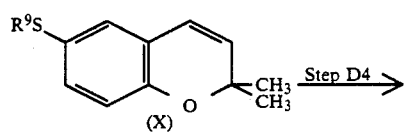

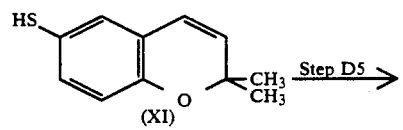

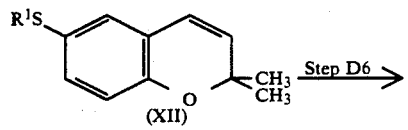

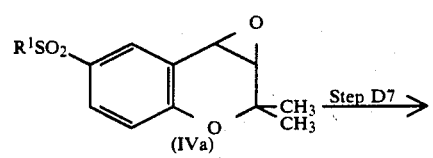

-continued
Reaction Scheme D:

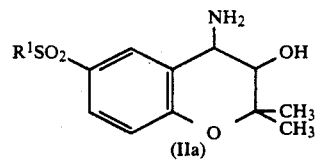

Reaction Scheme E:

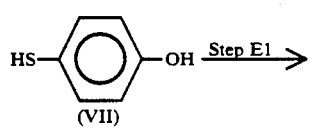

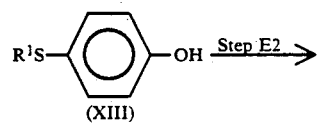

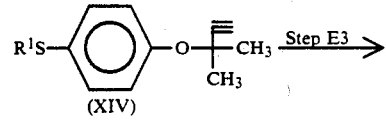

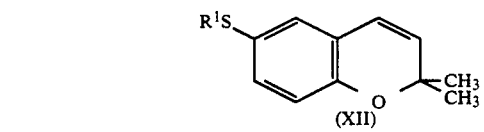

Reaction Scheme F:

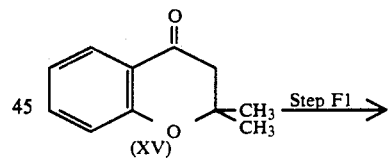

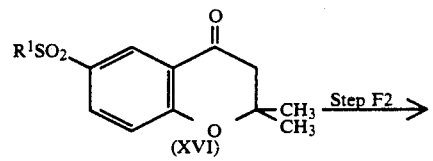

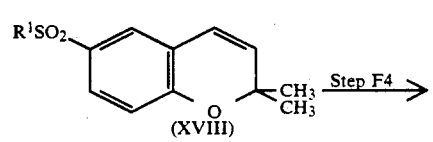

-continued
Reaction Scheme F:

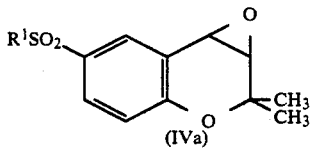

In the above formulae, $R^1$ is as defined above and $R^9$ represents an aralkyl group in which the alkyl part has from 1 to 4 carbon atoms and is substituted by one or more aryl groups, preferably from 1 to 3 such groups. The aryl groups are carbocyclic aryl groups having from 6 to 10, preferably 6 or 10, and most preferably 6, carbon atoms and are substituted or unsubstituted. The aralkyl group represented by $R^9$ is preferably a substituted or unsubstituted benzyl, diphenylmethyl (benzhydryl), triphenylmethyl (trityl), phenethyl, 1-phenylethyl, 2-phenylpropyl or 3-phenylpropyl group, more preferably a benzyl, methoxybenzyl, diphenylmethyl or triphenylmethyl group.

Reaction Scheme D

In Step D1 of Reaction Scheme D, an aralkylthiophenol of formula (VIII) can be prepared by treating 4-mercaptophenol, which has the formula (VII), with an alkali metal hydride (for example sodium hydride) in an inert solvent (for example an amide, such as dimethylform- amide, or an ether, such as tetrahydrofuran) and then reacting the resulting alkali metal salt with a compound of formula (XIX):

in which $R^9$ is as defined above and $X'$ represents a halogen atom. The reaction preferably takes place at a temperature of from 0° C. to room temperature and, under the preferred conditions, will normally require a period of from 30 minutes to 5 hours.

In Step D2 of Reaction Scheme D, a compound of formula (IX) can be prepared by reacting a compound of formula (VIII) with a compound of formula (XX):

(in which $X'$ is as defined above) in an inert solvent (for example: a ketone, such as acetone or methyl ethyl ketone, an alcohol, such as methanol or ethanol, or a mixture of any two or more of these solvents) and in the presence of a base (for example an alkali metal carbonate, such as sodium carbonate or potassium carbonate). The reaction preferably takes place at a temperature of from 50° C. to 100° C. and, under the preferred conditions, will normally require a period of from 10 hours to 60 hours. Alternatively, if necessary, iodine compounds (for example potassium iodide, sodium iodide or the like) may be present in the reaction mixture.

In Step D3 of Reaction Scheme D, a pyran compound of formula (X) can be prepared by treating the compound of formula (IX) at a temperature of from 100° C. to 200° C. for a period of 1 hour to 5 hours in an inert solvent (for example an aromatic hydrocarbon, such as toluene, chlorobenzene, dichlorobenzene or xylene).

In Step D4 of Reaction Scheme D, a mercapto compound of formula (XI) can be prepared by reacting the compound of formula (X) with a mercury salt (for example, mercuric trifluoroacetate or mercuric acetate) in an inert solvent (for example an aqueous organic carboxylic acid, such as aqueous acetic acid). The reaction preferably takes place at a temperature of from 0° C. to 50° C. and, under the preferred conditions, will normally require a period of from 30 minutes to 2 hours. The resulting mercury salt is then reacted with hydrogen sulfide or with a precursor of hydrogen sulfide (for example, sodium sulfide/hydrochloric acid). The reaction preferably takes place at a temperature of from 0° C. to 50° C. and, under the preferred conditions, will normally require a period of from 10 minutes to 1 hour. In the first of these steps, if necessary, a cationic stabilizers, such as anisole may also be present in the reaction mixture.

In Step D5 of Reaction Scheme D, a compound of formula (XII) can be prepared by reacting the compound of formula (XI) with a compound of formula (XXI):

(in which $R^1$ and $X'$ are as defined above) in an inert solvent (for example an amide, such as dimethylformamide, or an ether, such as tetrahydrofuran) in the presence of a base (for example an alkali metal hydride, such as sodium hydride, an alkali metal alkoxide, such as potassium t-butoxide, or an organic amine, such as triethylamine). The reaction preferably takes place at a temperature of from 0° C. to 50° C. and, under the preferred conditions, will normally require a period of from 2 hours to 10 hours. Alternatively, the reaction with a compound of formula (XXI) in which $R^1$ represents a trifluoromethyl group can be achieved by irradiation with ultraviolet radiation (for example, ultraviolet radiation generated from a mercury lamp), in the presence of an organic amine, such as ammonia or triethylamine, and in an inert solvent (for example liquid ammonia or an amide, such as dimethylformamide) at a relatively low temperature, preferably at a temperature of from −78° C. to room temperature, and preferably for a period of from 1 hour to 10 hours.

In Step D6 of Reaction Scheme D, a compound of formula (IVa), which may be one of the desired starting materials for use in the preparation of the compounds of the present invention, can be prepared by reacting the compound of formula (XII) with an oxidizing agent (for example a peroxide, such as 3-chloroperoxybenzoic acid, peracetic acid or hydrogen peroxide) in an inert solvent (for example a halogenated hydrocarbon, such as methylene chloride or dichloroethane). The reaction preferably takes place at a temperature of from 0° C. to 50° C. and, under the preferred conditions, will normally require a period of from 30 minutes to 3 hours. In this reaction, the desired compound of formula (IVa) is preferably prepared using about 3 moles or more of the oxidizing agent per mole of the compound of formula (XII).

In Step D7 of Reaction Scheme D, a compound of formula (IIa) can be prepared by reacting the compound of formula (IVa) with aqueous ammonia or with an ethanolic solution containing ammonia, preferably at a temperature of from 0° C. to 50° C. and preferably for a period of from 10 hours to 5 days.

Reaction Scheme E

Reaction Scheme E shows an alternative procedure for preparing the compound of formula (XII) obtained in Step D5 of Reaction Scheme D.

In Step E1 of Reaction Scheme E, thiophenol, which has the formula (VII), is reacted with a compound of formula (XXI) in a similar manner to that described in Step D5 of Reaction Scheme D, to prepare a compound of formula (XIII).

In Step E2 of Reaction Scheme E, a compound of formula (XIV) can be prepared by reacting the compound of formula (XIII) with a compound of formula (XX) in a similar manner to that described in Step D2 of Reaction Scheme D.

In Step E3 of Reaction Scheme E, a compound of formula (XII) can be prepared by reacting the compound of formula (XIV) in a similar manner to that described in Step D3 of Reaction Scheme D.

Reaction Scheme F

Reaction Scheme F shows an alternative procedure for preparing a compound of formula (IVa), which is one of the starting materials which may be used in the process of the present invention to prepare the compounds of the invention.

In Step F1 of Reaction Scheme F, a compound of formula (XVI) can be prepared by reacting the compound of formula (XV) with a compound of formula (XXII):

$$R^1SO_2\text{-}X' \quad \quad (XXII)$$

(in which $R^1$ and $X'$ are as defined above) in an inert solvent (for example a halogenated hydrocarbon, such as methylene chloride, or a nitrated hydrocarbon, such as nitromethane or nitrobenzene) and in the presence of a Lewis acid (for example aluminum oxide or ferric chloride). The reaction preferably takes place at a temperature of from 0° C. to 50° C. and, under the preferred conditions, will normally require a period of from 30 minutes to 24 hours.

In Step F2 of Reaction Scheme F, a compound of formula (XVII) can be prepared by reacting the compound of formula (XVI) with a reducing agent (for example, sodium borohydride or lithium aluminum hydride) in an inert solvent (for example methanol, aqueous ethanol, diethyl ether or tetrahydrofuran). The reaction preferably takes place at a temperature of from 0° C. to 40° C. and, under the preferred conditions, will normally require a period of from 0.5 hour to 3 hours.

In Step F3 of Reaction Scheme F, a compound of formula (XVIII) can be prepared by reacting the compound of formula (XVII) with a dehydrating agent (for example, pyridine/phosphorus oxychloride, pyridine/thionyl chloride or p-toluenesulfonic acid), preferably in an inert solvent (for example, pyridine or benzene). The reaction preferably takes place at a temperature of from −10° C. to 150° C. and, under the preferred conditions, will normally require a period of from 0.5 hour to 3 hours.

In Step F4 of Reaction Scheme F, a compound of formula (IVa) can be prepared by reacting the compound of formula (XVIII) in a similar manner to that described in Step D6 of Reaction Scheme D, followed by oxidation.

After completion of any of these reactions, the desired compounds produced by the reaction can be recovered from the reaction mixture by conventional means. For example, in one suitable recovery sequence, the solvent is distilled off from the reaction mixture, or the reaction mixture is poured into water, extracted with water-immiscible organic solvent and dried, after which the solvent is distilled off. The resulting residue may, if necessary, be further purified by conventional means, for example, recrystallization or the various chromatography techniques, notably column chromatography.

The compounds of the present invention have an excellent vasodilating activity as shown in the following Test Example. Accordingly, the compounds of the invention are expected to be very useful for the prophylaxis and therapy of a variety of disorders for which such activity is normally indicated, including, inter alia, the following diseases and disorders:

(1) hypertension, congestive heart failure, angina pectoris;

(2) reversible airway obstruction, asthma;

(3) peptic ulceration;

(4) local alopecia; and (5) incontinence;

and particularly for the treatment of cardiovascular diseases.

TEST EXAMPLE

Vasodilatory activity

A rat was sacrificed by phlebotomy. The thoracic aorta was immediately excised. After the connective tissue and adipose tissue had been removed, a helical strip preparation (in which the smooth blood vessels had been cut to form helical strips) was prepared. The preparation was suspended in a Magnus tube, and, after the preparation had become stable, phenylephrine ($1\times10^{-6}$M) was added to cause the blood vessels to contract. When the preparation had reached a stable state, a test sample containing the compound under investigation was applied cumulatively to observe the relaxing response. When the response reached a maximum, $10^{-4}$M of papaverine was added and the resulting induced response was regarded as 100%. The experiment was carried out using each test compound at several different doses. The relaxation values achieved at each of the doses (mol/l) were measured and the concentration of the test compound showing a 30% relaxation ($IC_{30}$ mol/l) was calculated.

In each test, Cromakalim and 3,4-dihydro-2,2-dimethyl-6-trifluoromethylsulfonyl-4-(2-oxo-1-pyrrolidinyl)-2H-1-benzopyran-3-ol (prior art compound B, referred to previously) were used as the control compounds. The relative activities are shown in Table 3. In the Table, the compounds of the invention are identified by the numbers of the Examples hereafter in which their preparation is demonstrated.

TABLE 3

| Test compound | Vasodilatory activity |
| --- | --- |
| | Relative activity |
| Compound of Example 1 | 17 |
| Compound of Example 6 | 61 |
| Compound of Example 12 | 48 |
| Compound of Example 13 | 64 |
| Cromakalim | 1 |
| Compound B | 9.6 |

It can be seen clearly from the above Table that the compounds of the present invention exerted a potent hypotensive effect. They also showed an excellent durability in a hypotensive test by oral administration in vivo to spontaneously hypertensive rats.

The compounds of the present invention can be used for the prophylaxis and therapy of cardiovascular and other disorders, including hypertension. For this purpose, they may, if required, be used in admixture with other active compounds and/or with common carriers, diluents, adjuvants and/or excipients, to form a pharmaceutical preparation. Alternatively, they may, if required, be administered alone. The form of the pharmaceutical preparation will, of course, depend upon the chosen route of administration, but, for oral administration, the compounds may, for example, be formulated as powders, granules, syrups, tablets or capsules; for parenteral administration, they may be formulated as injections or inhalations. Although the dosage may vary depending upon the symptoms of the patient, the nature and severity of the disease or disorder and the route and manner of administration, in the case of oral administration to an adult human patient, they may normally be administered at a daily dose of from 0.1 to 500 mg, particularly from 0.2 to 100 mg, and in the case of intravenous administration, they may normally be administered at a daily dose of from 0.02 to 100 mg, particularly from 0.1 to 30 mg. The compounds may be administered in a single dose, or in divided doses, for example twice a day.

The preparation of the compounds of the present invention is further illustrated by the following non-limiting Examples, whilst the preparation of certain of the starting materials used in these Examples is illustrated by the subsequent Preparations.

EXAMPLE 1 trans-3,4-Dihydro-4-(1,2-dihydro-2-oxo-1-pyridyl)-2,2-dimethyl-6-trifluoromethylsulfonyl-2H-1-benzopyran-3-ol (Compound No. 1-24)

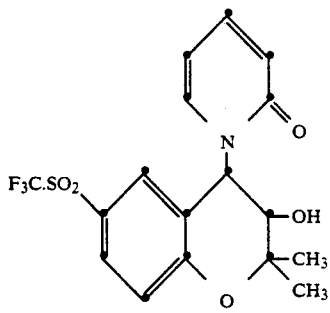

1.63 g of 2-trimethylsilyloxypyridine was added to a solution of 1.00 g of 3,4-epoxy-3,4-dihydro-2,2-dimethyl-6-trifluoromethylsulfonyl-2H-1-benzopyran (prepared as described in Preparation 8) in 1.2 ml of anhydrous tetrahydrofuran, and a solution of 2.54 g of tetrabutylammonium fluoride in anhydrous tetrahydrofuran was added to the resulting mixture through a syringe, whilst ice-cooling and under an atmosphere of nitrogen. The reaction mixture was stirred at room temperature for 72 hours, after which it was poured into water and extracted with ethyl acetate. The extract was then washed with water, with a 5% w/v aqueous solution of hydrochloric acid, with an aqueous solution of sodium hydrogencarbonate and with a saturated aqueous solution of sodium chloride, after which it was dried over anhydrous magnesium sulfate. The solvent was then removed by distillation under reduced pressure. The resulting residue was purified by column chromatography through silica gel, using a 2:1 by volume mixture of ethyl acetate and cyclohexane as the eluent, to afford 503 mg of the title compound as about a 1:1 mixture of rotational isomers, melting at 219°–220° C.

Nuclear Magnetic Resonance Spectrum (hexadeuterated dimethyl sulfoxide) δ ppm: 1.24 (3/2H, singlet); 1.32 (3/2H, singlet); 1.47 (3/2H, singlet); 1.52 (3/2H, singlet); 4.02–4.13 (1/2H, multiplet); 4.38–4.47 (1/2H, multiplet); 5.07 (1/2H, doublet, J=10 Hz); 5.95 (1H, doublet, J=6 Hz); 6.55 (1/2H, doublet, J=10 Hz); 6.1–6.4 (2H, multiplet); 7.0–7.9 (5H, multiplet).

Infrared Absorption Spectrum (KBr) $\nu_{max}$ cm$^{-1}$: 3270, 1663, 1580.

EXAMPLE 2 trans-3,4 Dihydro-4-(1,2-dihydro-2-oxo-1-pyridyl)-2,2-dimethyl-6-trifluoromethylsulfonyl-2H-1-benzopyran-3-ol (Compound No. 1-24)

105 mg of 2-hydroxypyridine were added to a suspension of 48 mg of sodium hydride (as a 55% w/w dispersion in mineral oil) in anhydrous dimethyl sulfoxide, and the resulting mixture was stirred at room temperature for 15 minutes. At the end of this time, 309 mg of 3,4-epoxy-3,4-dihydro-2,2-dimethyl-6-trifluoromethylsulfonyl-2H-1-benzopyran (prepared as described in Preparation 8) were added under an atmosphere of nitrogen and at room temperature to the mixture. The mixture was then stirred at room temperature for 24 hours, after which it was poured into water and extracted with ethyl acetate. The extract was washed with water and with a saturated aqueous solution of sodium chloride, in that order; it was then dried over anhydrous sodium sulfate. The solvent was then removed by distillation under reduced pressure, and the resulting residue was purified by column chromatography through silica gel, using a 3:1 by volume mixture of ethyl acetate and cyclohexane as the eluent, to afford 95 mg of the title compound.

The nuclear magnetic resonance and infrared spectra of the compound thus obtained were identical to those of the compound obtained as described in Example 1.

EXAMPLE 3

2,2-Dimethyl-4-(1-oxoisoindolin-2-yl)-6-trifluoromethylsulfonyl-2H-1-benzopyran (Compound No. 2-1)

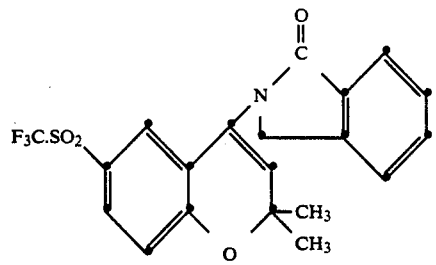

200 mg of soda talc (Merck Catalog No. 1567) were added to a solution of 200 mg of trans-3,4-dihydro-2,2-dimethyl-4-(1-oxoisoindolin-2-yl)-6-trifluoromethylsulfonyl-2H-1-benzopyran-3-ol (prepared as described in Preparation 13) in 6 ml of dioxane, and the resulting mixture was stirred for 30 minutes whilst heating it on an oil bath kept at 140° C. The reaction mixture was cooled and then freed from insoluble materials by filtration. The solvent was then removed by distillation under reduced pressure. The residue was dissolved in 20 ml of methylene chloride, and the resulting solution was washed with water and with a saturated aqueous solution of sodium chloride, in that order. The solution was dried over anhydrous magnesium sulfate, and then the solvent was removed by distillation under reduced pressure. The oily residue thus obtained was recrystallized from ethyl acetate, to afford 81 mg of the title compound, melting at 110°-115° C.

Nuclear Magnetic Resonance Spectrum (CDCl₃) δ ppm: 1.61 (6H, singlet); 4.65 (2H, singlet); 5.89 (1H, singlet); 7.07 (1H, doublet, J=8 Hz); 7.5-7.7 (4H, multiplet); 7.82 (1H, doublet of doublets, J=2 & 8 Hz); 7.94 (1H, doublet, J=8 Hz).

Infrared Absorption Spectrum (KBr) $v_{max}$ cm$^{-1}$: 1690.

Mass spectrum (m/e): 423 (M+).

EXAMPLE 4 trans-6-Heptafluoropropylsulfonyl-3,4-dihydro-2,2-dimethyl-4-(1-oxoisoindolin-2yl)-2H-1-benzopyran-3-ol (Compound No. 1-3)

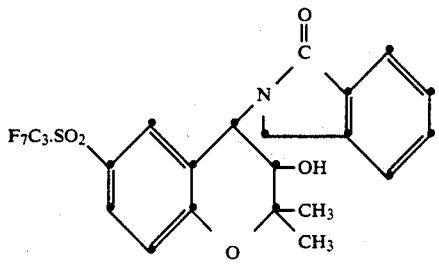

A solution of 0.142 g of zinc chloride and 0.065 g of sodium cyanoborohydride in 3 ml of methanol was added to a solution of 0.40 g of trans-4-amino-6-heptafluoropropylsulfonyl-3,4-dihydro-2,2-dimethyl-2H-1-benzopyran-3-ol (prepared as described in Preparation 4) and 0.156 g of methyl 2-formylbenzoate in 6 ml of methanol, and the resulting mixture was stirred at room temperature for 1 hour and then at 50° C. for 24 hours. At the end of this time, the mixture was cooled with ice and then mixed with a saturated aqueous solution of sodium hydrogencarbonate. The methanol was then removed by distillation under reduced pressure, and the resulting residue was diluted with water and extracted with methylene chloride. The extract was washed with water and with a saturated aqueous solution of sodium chloride, in that order, and dried over anhydrous magnesium sulfate; the solvent was then removed by distillation under reduced pressure. The resulting residue was recrystallized from ethyl acetate, to afford 0.356 g of the title compound, melting at 241°-249° C.

Nuclear Magnetic Resonance Spectrum (hexadeuterated dimethyl sulfoxide) δ ppm: 1.32 (3H, singlet); 1.54 (3H, singlet); 3.9-4.2 (2H, multiplet); 4.59 (1H, doublet, J=17 Hz); 5.32 (1H, broad singlet); 5.98 (1H, doublet, J=6 Hz); 7.24 (1H, doublet, J=9 Hz); 7.37 (1H, broad singlet); 7.5-7.7 (3H, multiplet); 7.80 (1H, doublet, J=7 Hz); 7.89 (1H, doublet of doublets, J=2 & 9 Hz).

Infrared Absorption Spectrum (KBr) $v_{max}$ cm$^{-1}$: 3478, 1667.

Mass spectrum (m/e): 541 (M+).

EXAMPLE 5

6-Heptafluoropropylsulfonyl-2,2-dimethyl-4-(1-oxoisoindolin-2-yl) 2H-1-benzopyran (Compound No. 2-3)

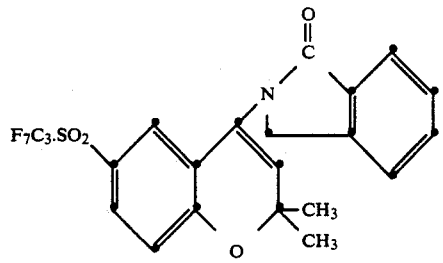

Following a procedure similar to that described in Example 3, but using 100 mg of trans-6-heptafluoropropylsulfonyl-3,4-dihydro-2,2-dimethyl-4-(1-oxoisoindolin-2-yl) 2H-1-benzopyran-3-ol (prepared as described in Preparation 4) and 100 mg of soda talc, 30 mg of the title compound, melting at 164°-166° C., were obtained.

Nuclear Magnetic Resonance Spectrum (CDCl₃) δ ppm: 1.61 (6H, singlet); 4.64 (2H, singlet); 5.89 (1H, singlet); 7.07 (1H, doublet, J=9 Hz); 7.5-7.7 (4H, multiplet); 7.82 (1H, doublet of doublets, J=2 & 9 Hz); 7.95 (1H, doublet, J=7 Hz).

Infrared Absorption Spectrum (KBr) $v_{max}$ cm$^{-1}$: 1686.

Mass spectrum (m/e): 523 (M+).

EXAMPLE 6 trans-4-(1,2-Dihydro-2-oxo-1-pyridyl)-2,2-dimethyl-6-trifluoromethylsulfonyl-2H-1-benzopyran Compound No. 2-11)

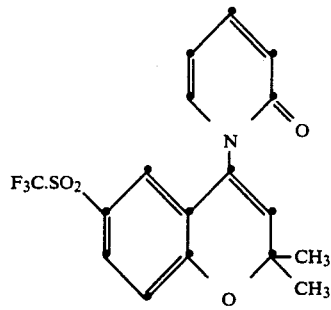

Following a procedure similar to that described in Example 3, but using 406 mg of trans-3,4 dihydro-4-(1,2-dihydro-2-oxo-1-pyridyl)-2,2-dimethyl-6-trifluoromethylsulfonyl-2H-1-benzopyran-3-ol (prepared as described in Example 1) and 406 mg of soda talc (Merck Cat. No. 1657), 124 mg of the title compound, melting at 214°-215° C., were obtained.

Nuclear Magnetic Resonance Spectrum (CDCl₃) δ ppm: 1.60 (3H, singlet); 1.67 (3H, singlet); 5.86 (1H, singlet); 6.28 (1H, doublet of triplets, J=1 & 7 Hz); 6.66 (1H, doublet, J=9 Hz); 7.06 (1H, doublet, J=9 Hz); 7.15 (1H, doublet of doublets, J=2 & 7 Hz); 7.27 (1H, doublet, J=2 Hz); 7.46 (1H, multiplet); 7.82 (1H, doublet of doublets, J=2 & 9 Hz).

Mass spectrum (m/e): 385 (M+).

EXAMPLE 7 trans-3,4-Dihydro-2,2-dimethyl-4-(1-oxoisoindolin-2-yl)-6-trifluoromethylsulfonyl-2H-1-benzopyran-3-yl nitrate (Compound No. 1-5)

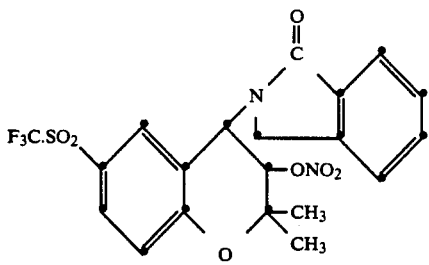

116 mg of nitronium tetrafluoroborate were added to a solution of 300 mg of trans-3,4-dihydro-2,2-dimethyl-4-(1-oxoisoindolin-2-yl)-6-trifluoromethylsulfonyl-2H-1-benzopyran-3-ol (prepared as described in Preparation 13) in 5 ml of methylene chloride, and the resulting mixture was stirred at room temperature for 1.5 hours. At the end of this time, the reaction mixture was diluted with 20 ml of water and extracted with 15 ml of methylene chloride. The extract was washed with water and with a saturated aqueous solution of sodium chloride, in that order, after which it was dried over anhydrous magnesium sulfate. The solvent was then removed by distillation under reduced pressure, and the resulting residue was purified by column chromatography through silica gel, using a 1:4 by volume mixture of ethyl acetate and cyclohexane as the eluent, to afford 88 mg of the title compound as crystals, melting at 189.5°-190° C.

Nuclear Magnetic Resonance Spectrum (CDCl$_3$) $\delta$ ppm: 1.48 (3H, singlet); 1.61 (3H, singlet); 4.06 (1H, doublet, J=17 Hz); 4.33 (1H, doublet, J=17 Hz); 5.54 (1H, doublet, J=10 Hz); 5.92 (1H, doublet, J=10 Hz); 7.17 (1H, doublet, J=9 Hz); 7.4-7.6 (4H, multiplet); 7.8-8.0 (2H, multiplet).

Mass spectrum (m/e): 440 (M$^+$- NO$_2$), 423 (M$^+$- HNO$_3$).

EXAMPLE 8 trans-3,4-Dihydro-4-(1,2-dihydro-3-methyl-2-oxo-1-pyridyl)-2,2-dimethyl 6-trifluoromethylsulfonyl 2H-1-benzopyran-3-ol (Compound No. 1-41)

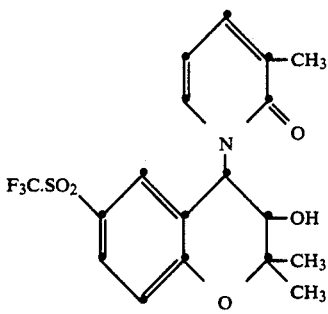

441 mg of 3-methyl-2-trimethylsilyloxypyridine were added to a solution of 200 mg of 3,4-epoxy-3,4-dihydro-2,2-dimethyl-6-trifluoromethylsulfonyl-2H-1-benzopyran (prepared as described in Preparation 8) in 0.2 ml of anhydrous tetrahydrofuran. Subsequently a solution of 509 mg of tetrabutylammonium fluoride in anhydrous tetrahydrofuran was added to the resulting mixture, whilst ice-cooling and under an atmosphere of nitrogen. The reaction mixture was then stirred at room temperature for 5 days, after which it was worked up in a similar manner to that described in Example 1. The product was then purified by column chromatography through silica gel, using a 1:2 by volume mixture of ethyl acetate and cyclohexane as the eluent, to give 135 mg of the title compound, melting at 215°-216° C.

Nuclear Magnetic Resonance Spectrum (CDCl$_3$), $\delta$ ppm: 1.41 (3H, singlet); 1.58 (3H, singlet); 1.0-2.2 (1H, broad); 2.24 (3H, singlet); 3.88 (1H, doublet, J=10 Hz); 6.19 (1H, triplet, J=7 Hz); 6.48 (1H, doublet, J=10 Hz); 6.71 (1H, doublet, J=7 Hz); 7.14 (1H, doublet, J=9 Hz); 7.28 (1H, doublet, J=7 Hz); 7.46 (1H, broad singlet); 7.87 (1H, doublet of doublets, J=2 & 9 Hz).

Infrared Absorption Spectrum (KBr), $\nu_{max}$ cm$^{-1}$: 3324, 1652, 1590, 1361.

Mass Spectrum (m/e): 418 (M$^+$+1).

EXAMPLE 9 trans-3,4-Dihydro-4-(1,2-dihydro-3-methoxy-2-oxo-1-pyridyl)-2,2-dimethyl-6-trifluoromethylsulfonyl-2H-1-benzopyran-3-ol (Compound No. 1-42)

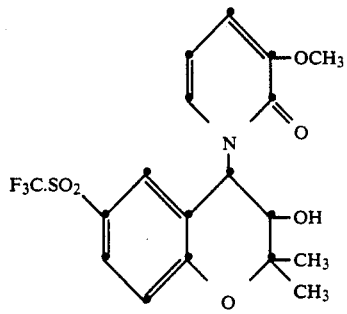

98 mg of 3-methoxy-2(1H)-pyridone were added to a suspension of 38 mg of sodium hydride (as a 55% w/w dispersion in mineral oil) in 3 ml of dimethyl sulfoxide, and the resulting mixture was stirred at room temperature for 30 minutes. At the end of this time, a solution of 200 mg of 3,4-epoxy-3,4-dihydro-2,2-dimethyl-6-trifluoromethylsulfonyl-2H-1-benzopyran (prepared as described in Preparation 8) in 1.5 ml of dimethyl sulfoxide was added at the same temperature and under an atmosphere of nitrogen. The reaction mixture was stirred at room temperature for 4 days, after which it was worked up in a similar manner to that described in Example 2. The product was then purified by column chromatography through silica gel, using a 1:2 by volume mixture of ethyl acetate and cyclohexane as the eluent, to give 16 mg of the title compound, melting at 223°-225° C.

Nuclear Magnetic Resonance Spectrum (CDCl$_3$), $\delta$ ppm: 1.42 (3H, singlet); 1.58 (3H, singlet); 3.75 (1H, doublet, J=5 Hz); 3.88 (1H, doublet of doublets, J=5 & 10 Hz); 3.90 (3H, singlet); 6.20 (1H, triplet, J=7 Hz); 6.43 (1H, doublet of doublets, J=1.5 & 7 Hz); 6.50 (1H, doublet, J=10 Hz); 6.69 (1H, doublet of doublets, J=1.5 & 7 Hz); 7.13 (1H, doublet, J=9 Hz); 7.45 (1H, broad singlet); 7.86 (1H, doublet of doublets, J=2 & 9 Hz).

Infrared Absorption Spectrum (KBr), $\nu_{max}$ cm$^{-1}$: 3312, 1655, 1603, 1371.

Mass Spectrum (m/e): 433 (M$^+$).

EXAMPLE 10 trans-3,4-Dihydro-2,2-dimethyl-4-(6-nitro 1-oxoisoindolin-2-yl)-6-trifluoromethylsulfonyl-2H-1-benzopyran-3-ol (Compound No. 1-15)

A solution of 0.164 g of zinc chloride and 0.075 g of sodium cyanoborohydride in 3.3 ml of propanol was added to a solution of 0.326 g of trans-4-amino-3,4-dihydro-2,2-dimethyl-6-trifluoromethylsulfonyl 2H-1-benzopyran-3-ol (prepared from its hydrochloride prepared as described in Preparation 9) and 0.224 g of methyl 2-formyl-5-nitrobenzoate in 3.3 ml of propanol, and the resulting mixture was heated under reflux in an oil bath kept at 140° C. for 1.5 hours. At the end of this time, the reaction mixture was diluted with 150 ml of ethyl acetate, and the resulting solution was washed with 1N aqueous hydrochloric acid, with water, with a saturated aqueous solution of sodium hydrogencarbonate and with a saturated aqueous solution of sodium chloride, in that order. The mixture was then dried over anhydrous sodium sulfate, after which the solvent was removed by distillation under reduced pressure. The resulting residue was recrystallized from a mixture of ethyl acetate and hexane to give 0.424 g of the title compound, melting at 264°-266° C.

Nuclear Magnetic Resonance Spectrum (hexadeuterated dimethyl sulfoxide), δ ppm: 1.34 (3H, singlet); 1.54 (3H, singlet); 3.86–4.24 (1H, multiplet); 4.26 (1H, doublet, J=20 Hz); 4.84 (1H, doublet, J=20 Hz); 5.38 (1H, doublet, J=10 Hz); 5.86–6.16 (1H, multiplet); 7.14 (1H, doublet, J=10 Hz); 7.46–7.60 (2H, multiplet); 7.80–8.14 (2H, multiplet); 8.44–8.74 (2H, multiplet).

Infrared Absorption Spectrum (KBr), $\nu_{max}$ cm$^{-1}$: 3300, 1680.

Mass Spectrum (m/e): 487 (M$^+$+1).

Elemental analysis: Calculated for $C_{20}H_{17}F_3N_2O_7S$: C, 49.38%; H, 3.52%; N, 5.76%; F, 11.72%; S, 6.59%. Found: C, 49.78%; H, 3.84%; N, 5.38%; F, 11.69%; S, 6.74%.

EXAMPLE 11 trans-3,4-Dihydro-2.2-dimethyl-4-(7-nitro-1-oxoisoindolin-2-yl)-6-trifluoromethylsulfonyl-2H-1-benzopyran-3-ol (Compound No. 1-14)

Following the procedure and working up described in Example 10, but using 0.326 g of trans-4-amino-3,4-dihydro-2,2-dimethyl-6-trifluoromethylsulfonyl-2H-1-benzopyran-3-ol (prepared from its hydrochloride, in turn prepared as described in Preparation 9), 0.224 g of methyl 2-formyl-6-nitrobenzoate, 0.164 g of zinc chloride and 0.075 g of sodium cyanoborohydride, 0.391 g of the title compound, melting at 283°-284° C., were obtained.

Nuclear Magnetic Resonance Spectrum (hexadeuterated dimethyl sulfoxide), δ ppm: 1.34 (3H, singlet); 1.54 (3H, singlet); 3.46 (1H, broad singlet); 4.02 (1H, doublet, J=10 Hz); 4.22 (1H, doublet, J=18 Hz); 4.76 (1H, doublet, J=18 Hz); 5.34 (1H, doublet, J=10 Hz); 7.29 (1H, doublet, J=8 Hz); 7.46–7.62 (1H, multiplet); 7.76–8.02 (4H, multiplet).

Infrared Absorption Spectrum (KBr), $\nu_{max}$ cm$^{-1}$: 3440, 1670.

Mass Spectrum (m/e): 486 (M$^+$).

Elemental analysis: Calculated for $C_{20}H_{17}F_3N_2O_7S$: C, 49.39%; H, 3.52%; N, 5.76%; F, 11.72%; S, 6.59%. Found: C, 49.43%; H, 3.50%; N, 5.78%; F, 11.59%; S, 6.58%.

EXAMPLE 12 trans-3,4-Dihydro-2,2 dimethyl-4-(4-nitro-1-oxoisoindolin-2-yl)-6-trifluoromethylsulfonyl-2H-1-benzopyran-3-ol (Compound No. 1-13)

0.362 g of trans-4 amino-3,4-dihydro-2,2-dimethyl-6-trifluoromethylsulfonyl-2H-1-benzopyran-3-ol (prepared from its hydrochloride, in turn prepared as described in Preparation 9) and 0.30 ml of triethylamine were added to a solution of 0.367 g of ethyl 2-bromomethyl-3-nitrobenzoate in 7.4 ml of dimethylformamide, and the resulting mixture was stirred at 100° C. for 1 hour in an atmosphere of nitrogen. The reaction mixture was then stirred under reflux of the solvent (at 152° C.) for a further 1 hour, after which the mixture was poured into dilute aqueous hydrochloric acid and extracted with ethyl acetate. The extract was then washed with water, with a saturated aqueous solution of sodium hydrogencarbonate and a with saturated aqueous solution of sodium chloride, after which it was dried over anhydrous sodium sulfate. The solvent was then removed by distillation under reduced pressure, and the residue was purified by column chromatography through silica gel, using a 1:1:1 by volume mixture of ethyl acetate, cyclohexane and tetrahydrofuran as the eluent. The product obtained from the eluate was recrystallized from a mixture of tetrahydrofuran and hexane to give 0.295 g of the title compound, melting at 292°-295° C.

Nuclear Magnetic Resonance Spectrum (hexadeuterated dimethyl sulfoxide), δ ppm: 1.34 (3H, singlet); 1.54 (3H, singlet); 4.14 (1H, doublet of doublets, J=6 & 10 Hz); 4.58 (1H, doublet, J=18 Hz); 5.18 (1H, doublet, J=18 Hz); 5.38 (1H, doublet, J=10 Hz); 5.92 (1H, doublet, J=6 Hz); 7.22 (1H, doublet, J=8 Hz); 7.48–7.64 (1H, multiplet) 7.74–8.06 (2H, multiplet); 8.28 (1H, doublet, J=8 Hz); 8.54 (1H, doublet of doublets, J=2 & 8 Hz).

Infrared Absorption Spectrum (KBr), $\nu_{max}$ cm$^{-1}$: 3460, 1676.

Mass Spectrum (m/e): 468 (M$^+$- 18).

Elemental analysis: Calculated for $C_{20}H_{17}F_3N_2O_7S$: C, 49.39%; H, 3.52%; N, 5.76%; F, 11.72%; S, 6.59%. Found: C, 49.49%; H, 3.69%; N, 5.72%; F, 11.69%; S, 6.58%.

EXAMPLE 13 trans-4-(4-Fluoro-1-oxoisoindolin-2-yl)-3,4-dihydro-2,2-dimethyl-6-trifluoromethylsulfonyl-2H-1-benzopyran-3-ol (Compound No. 1-16)

Following the procedure and working up described in Example 12, but using 0.272 g of methyl 2-bromomethyl-3-fluorobenzoate, 0.326 g of trans-4-amino-3,4-dihydro-2,2-dimethyl 6-trifluoromethylsulfonyl-2H-1-benzopyran- 3-ol and 0.15 ml of triethylamine, 0.294 g of the title compound, melting at 259°-261° C., was obtained after purification by column chromatography through silica gel, using a 1:1 by volume mixture of cyclohexane and ethyl acetate as the eluent, followed by recrystallization from a mixture of ethyl acetate and hexane.

Nuclear Magnetic Resonance Spectrum (hexadeuterated dimethyl sulfoxide), δ ppm: 1.34 (3H, singlet); 1.54 (3H, singlet); 4.08 (1H, doublet, J=10 Hz); 4.16 (1H, doublet, J=18 Hz); 4.76 (1H, doublet, J=18 Hz); 5.36 (1H, doublet, J=10 Hz); 5.90 (1H, broad singlet); 7.20 (1H, doublet, J=8 Hz); 7.36–8.02 (5H, multiplet).

Infrared Absorption Spectrum (KBr), $v_{max}$ cm$^{-1}$: 3460, 1670.

Mass Spectrum (m/e): 460 (M$^+$ +1).

Elemental analysis: Calculated for C$_{20}$H$_{17}$F$_4$NO$_5$S: C, 52.29%; H, 3.73%; N, 3.05%; F, 16.54%; S, 6.98%. Found: C, 52.29%; H, 3.88%; N, 3.05%; F, 16.81%; S, 7.30%.

PREPARATION 1

4-(Heptafluoropropyl)thiophenol 3.16 g of 4-hydroxythiophenol were added, whilst ice-cooling, to a suspension of 2.40 g of sodium hydride (as a 55% w/w dispersion in mineral oil) in 64 ml of dimethylformamide, under an atmosphere of nitrogen, and the resulting mixture was stirred for 15 minutes. 3.6 ml of heptafluoropropyl 1-iodide were then added to the mixture, which was then stirred at room temperature for 5 hours. At the end of this time, the reaction mixture was poured into dilute aqueous hydrochloric acid and extracted with ethyl acetate. The extract was washed with water, with a saturated aqueous solution of sodium hydrogencarbonate and with a saturated aqueous solution of sodium chloride, in that order, after which the solvent was removed by distillation under reduced pressure. The resulting residue was purified by column chromatography through silica gel, using a 1:1 by volume mixture of cyclohexane and ethyl acetate as the eluent, to afford 3.40 g of the title compound.

Nuclear Magnetic Resonance Spectrum (CDCl$_3$) δ ppm: 5.87 (1H, broad singlet); 6.85 (2H, doublet, J=9 Hz); 7.52 (2H, doublet, J=9 Hz).

Mass spectrum (m/e): 294 (M$^+$).

PREPARATION 2

6-(Heptafluoropropylthio)-2,2-dimethyl 2H-1-benzopyran 11 ml of a dioxane solution of 3.40 g of 4-(heptafluoropropyl)thiophenol (prepared as described in Preparation 1), 1.85 g of 3-chloro-3-methyl-1-butyne and 2.50 g of a 40% w/v aqueous solution of trimethylbenzylammonium hydroxide, were added to 10.8 ml of an aqueous solution containing 0.72 g of sodium hydroxide, and the resulting mixture was heated under reflux for 15 hours. At the end of this time, the reaction mixture was poured into water and extracted with ethyl acetate. The extract was washed with a dilute aqueous solution of sodium hydroxide, with water, with dilute aqueous hydrochloric acid and with a saturated aqueous solution of sodium chloride, in that order, after which it was dried over anhydrous sodium sulfate. The solvent was then removed by distillation under reduced pressure, to give 3.81 g of oily material as a residue. The whole of this was dissolved in 16 ml of dichlorobenzene, and the resulting solution was heated under reflux for 2 hours under an atmosphere of nitrogen. The solvent was then stripped from the reaction mixture by distillation under reduced pressure, and the resulting residue was purified by column chromatography through silica gel, using cyclohexane as the eluent, to afford 1.67 g of the title compound.

Nuclear Magnetic Resonance Spectrum (CDCl$_3$) δ ppm: 1.42 (6H, singlet); 5.64 (1H, doublet, J=10 Hz); 6.30 (1H, doublet, J=10 Hz); 7.20–7.46 (2H, multiplet); 6.78 (1H, doublet, J=9 Hz).

PREPARATION 3

3,4-Epoxy-6-heptafluoropropylsulfonyl-3,4-dihydro-2,2-dimethyl-2H-1-benzopyran 2.79 g of 3-chloroperoxybenzoic acid (of 85% purity) were added to a solution of 1.65 g of 6-heptafluoropropylthio-2,2-dimethyl-2H-1-benzopyran (prepared as described in Preparation 2) in 33 ml of methylene chloride, and the resulting mixture was stirred at room temperature for 1.5 hours. At the end of this time, the reaction mixture was diluted with ethyl acetate and then washed with a 1N aqueous solution of sodium hydroxide, with water and with a saturated aqueous solution of sodium chloride, in that order. The solution was dried over anhydrous sodium sulfate, and then the residue obtained by distilling off the solvent under reduced pressure was purified by column chromatography through silica gel, using a 5:1 by volume mixture of cyclohexane and ethyl acetate as the eluent, to afford 1.21 g of the title compound.

Nuclear Magnetic Resonance Spectrum (CDCl$_3$) δ ppm: 1.32 (3H, singlet); 1.60 (3H, singlet); 3.66 (1H, doublet, J=4 Hz); 3.98 (1H, doublet, J=4 Hz); 7.00 (1H, doublet, J=8 Hz); 7.90 (1H, doublet of doublets, J=8 & 2 Hz); 8.05 (1H, doublet, J=2 Hz).

Infrared Absorption Spectrum (liquid film) $v_{max}$ cm$^{-1}$: 1330, 1100.

Mass spectrum (m/e): 408 (M$^+$).

PREPARATION 4 trans-4-Amino-6-heptafluoropropylsulfonyl-3,4-dihydro-2,2-dimethyl-2H-1-benzopyran-3-ol 30 ml of 28% v/v aqueous ammonia were added to a solution of 1.086 g of 3,4-epoxy-6-heptafluoropropylsulfonyl-3,4-dihydro-2,2-dimethyl-2H-1-benzopyran (prepared as described in Preparation 3) in 30 ml of ethanol, and the resulting mixture was allowed to stand at room temperature for 3 days. At the end of this time, the reaction mixture was poured into water and extracted with methylene chloride. The extract was washed with water and dried over anhydrous sodium sulfate. The solvent was removed by distillation under reduced pressure, and then the resulting residue was purified by column chromatography through silica gel, using a 1:1 by volume mixture of cyclohexane and ethyl acetate as the eluent. The fractions containing the desired compound were then recrystallized from a mixture of ethyl acetate and hexane, to afford 0.796 g of the title compound, melting at 176°–177° C.

Nuclear Magnetic Resonance Spectrum (CDCl$_3$) δ ppm: 1.26 (3H, singlet); 1.54 (3H, singlet); 1.80–2.50 (3H, multiplet); 3.34 (1H, doublet, J=10 Hz); 3.74 (1H, doublet, J=10 Hz); 6.98 (1H, doublet, J=8 Hz); 7.80 (1H, doublet of doublets, J=8 & 2 Hz); 8.12 (1H, doublet, J=2 Hz).

Infrared Absorption Spectrum (KBr) $v_{max}$ cm$^{-1}$: 3140.

Mass spectrum (m/e): 426 (M$^+$ +1).

Elemental analysis: Calculated for C$_{14}$H$_{14}$F$_7$NO$_4$S: C, 39.54%; H, 3.32%; N, 3.29%; F, 31.27%; S, 7.54%. Found: C, 39.85%; H, 3.51%; N, 3.26%; F, 31.23%; S, 7.33%.

PREPARATION 5

6-(4-Methoxybenzylthio)-2,2-dimethyl-2H-1-benzopyran

5(a) 4-(4-methoxybenzylthio)phenol

A solution of 50.47 g of p-hydroxythiophenol in 250 ml of tetrahydrofuran was added to a suspension of 38.40 g of sodium hydride (as a 55% w/w dispersion in mineral oil) in 380 ml of dimethylformamide, whilst ice-cooling, and under an atmosphere of nitrogen, and the resulting mixture was stirred for 0.5 hour. At the end of this time, a solution of 54.2 ml of p-methoxybenzyl chloride in 120 ml of tetrahydrofuran was added dropwise to the resulting mixture, which was then stirred for 1 hour. The reaction mixture was then neutralized by adding acetic acid, whilst ice-cooling, after which it was poured into water. The mixture was then extracted with ethyl acetate, and the extract was washed with water and with a saturated aqueous solution of sodium chloride, in that order. The resulting solution was then dried, after which the solvent was removed by distillation under reduced pressure, and the residue was purified by column chromatography through silica gel, using a 1:3 by volume mixture of cyclohexane and tetrahydrofuran as the eluent. The eluted product was recrystallized from a mixture of tetrahydrofuran and hexane, to afford 88.99 g of the title compound.

Infrared Absorption Spectrum (Nujol, trade mark), $\nu_{max}$ cm$^-$: 3380, 1450, 1250.

5(b) 6-(4-Methoxybenzylthio)-2,2-dimethyl-2H-1-benzopyran

A solution of 73.84 g of 3-chloro-3-methyl-1-butyne in 225 ml of methanol, 11.95 g of potassium iodide and 99.50 g of potassium carbonate was added to the whole of the 4-(4-methoxybenzylthio)phenol prepared as described in step (a) above in 0.9 liters of methyl ethyl ketone, and the resulting mixture was heated under reflux for 40 hours in an atmosphere of nitrogen. At the end of this time, the reaction mixture was extracted with ethyl acetate, and the extract was washed with water and with a saturated aqueous solution of sodium chloride, in that order. It was then dried over anhydrous sodium sulfate, after which the solvent was removed by distillation under reduced pressure. The residue was purified by column chromatography through silica gel, using a 5:1 by volume mixture of cyclohexane and ethyl acetate as the eluent, to afford 67.68 g of an ether as an oil. A solution of the whole of this ether in 340 ml of o-dichlorobenzene was then heated under reflux for 2 hours in an atmosphere of nitrogen. At the end of this time, the reaction mixture was freed from the solvent by distillation under reduced pressure, and the residue was purified by column chromatography through silica gel, using a 20:1 by volume mixture of cyclohexane and ethyl acetate as the eluent. The eluted product was recrystallized from hexane to afford 48.74 g of the title compound, melting at 58°-59° C.

Nuclear Magnetic Resonance Spectrum (CDCl$_3$) δ ppm: 1.38 (6H, singlet); 3.72 (3H, singlet); 3.90 (2H, singlet); 5.56 (1H, doublet, J=10 Hz); 6.22 (1H, doublet, J=10 Hz); 6.58-7.28 (7H, multiplet).

Mass spectrum (m/e): 312 (M$^+$).

Elemental analysis: Calculated for C$_{19}$H$_{20}$O$_2$S: C, 73.04%; H, 6.45%; S, 10.26%. Found: C, 73.33%; H, 6.49%; S, 10.39%.

PREPARATION 6

6-Mercapto-2,2-dimethyl-2H-1-benzopyran 0.313 g of 6-(4-methoxybenzylthio)-2,2-dimethyl-2H-1-benzopyran was dissolved in 12 ml of 80% acetic acid, with heating, and 0.12 ml of anisole and 0.512 g of mercuric trifluoroacetate were added to the resulting solution. The resulting mixture was stirred at 40° C. for 1 hour, after which the reaction mixture was extracted with ethyl acetate. The extract was washed with water, with an aqueous solution of sodium hydrogencarbonate and with a saturated aqueous solution of sodium chloride, in that order, after which it was dried over anhydrous sodium sulfate. The solvent was then removed by distillation under reduced pressure, and the residue was purified by column chromatography through silica gel, using a 5:1 by volume mixture of cyclohexane and ethyl acetate as the eluent. The eluted product was reprecipitated from a mixture of hexane and ethyl acetate to afford 0.283 g of the mercuric salt of the title compound as crystals.

Nuclear Magnetic Resonance Spectrum (CDCl$_3$) δ ppm: 1.40 (6H, singlet); 5.58 (1H, doublet, J=10 Hz); 6.20 (1H, doublet, J=10 Hz); 6.60 (1H, doublet, J=8 Hz); 7.02-7.28 (2H, multiplet).

Mass spectrum (m/e): 584 (M$^+$+1).

48 ml of an aqueous solution of 4.80 g of sodium sulfide nonahydrate were then added dropwise to a solution of 2.33 g of this mercuric salt in a mixture of 46 ml of tetrahydrofuran and 46 ml of methanol, and 4.0 ml of concentrated hydrochloric acid were added to the resulting mixture, whilst ice-cooling. The mixture was then stirred at room temperature for 0.5 hour, after which it was freed from insoluble materials by filtration with the aid of active charcoal. The filtrate was extracted with ethyl acetate. The extract was washed with water, with an aqueous solution of sodium hydrogencarbonate and with a saturated aqueous solution of sodium chloride, in that order, after which it was dried over anhydrous sodium sulfate. The solvent was then removed by distillation under reduced pressure, to afford 1.47 g of the title compound as an oil.

Nuclear Magnetic Resonance Spectrum (CDCl$_3$) δ ppm: 1.42 (6H, singlet); 3.28 (1H, singlet); 5.58 (1H, doublet, J=10 Hz); 6.22 (1H, doublet, J=10 Hz); 6.64 (1H, doublet of doublets, J=8 & 2 Hz); 6.92-7.30 (2H, multiplet).

Mass spectrum (m/e): 192 (M$^+$).

PREPARATION 7

2,2-Dimethyl-6-trifluoromethylthio-2H-1-benzopyran 1.45 g of 6-mercapto-2,2-dimethyl-2H-1-benzopyran (prepared as described in Preparation 6) was suspended in 30 ml of liquid ammonia, and 8.23 g of trifluoromethyl iodide were then added to the suspension at −60° C. in an atmosphere of nitrogen. The resulting mixture was then irradiated at −65° C. for 2 hours and then at 25° C. for 2 hours, using a low pressure mercury lamp. At the end of this time, the reaction mixture was diluted with ethyl acetate and washed with dilute aqueous hydrochloric acid, with water, with an aqueous solution of sodium hydrogencarbonate and with a saturated aqueous solution of sodium chloride, in that order. The organic layer was then dried over anhydrous sodium sulfate and concentrated by distillation under reduced pressure. The resulting residue was purified by column chromatography through silica gel, using a 20:2:1 by volume mixture of cyclohexane, chloroform and ethyl acetate as the eluent, to afford 1.17 g of the title compound as an oil.

Nuclear Magnetic Resonance Spectrum (CDCl$_3$) δ ppm: 1.46 (6H, singlet); 5.62 (1H, doublet, J=10 Hz); 6.28 (1H, doublet, J=10 Hz); 6.76 (1H, doublet, J=8 Hz); 7.20–7.46 (2H, multiplet).

Mass spectrum (m/e): 260 (M+).

PREPARATION 8

3,4-Epoxy-3,4-dihydro-2,2 dimethyl-6-trifluoromethylsulfonyl-2H-1-benzopyran Following a procedure similar to that described in Preparation 3, but using 1.15 g of 2,2 dimethyl-6-trifluoromethylthio-2H-1-benzopyran (prepared as described in Preparation 7) and 4.59 g of 3-chloroperoxybenzoic acid (70% purity), 0.74 g of the title compound were obtained as an oil.

Nuclear Magnetic Resonance Spectrum (CDCl$_3$) δ ppm: 1.32 (3H, singlet); 1.60 (3H, singlet); 3.56 (1H, doublet, J=4 Hz); 4.00 (1H, doublet, J=4 Hz); 7.02 (1H, doublet, J=8 Hz); 7.92 (1H, doublet of doublets, J=8 & 2 Hz); 8.06 (1H, doublet, J=2 Hz).

Mass spectrum (m/e): 308 (M+).

PREPARATION 9 trans-4-Amino-3,4-dihydro-2,2-dimethyl-6-trifluoromethylsulfonyl-2H-1-benzopyran-3-ol hydrochloride Following a procedure similar to that described in Preparation 4, but using 0.68 g of 3,4-epoxy-3,4-dihydro-2,2-dimethyl-6-trifluoromethylsulfonyl-2H-1-benzopyran (prepared as described in Preparation 8) and 28% v/v aqueous ammonia, 0.55 g of the title compound were obtained as crystals, melting at 256°–259° C.

Nuclear Magnetic Resonance Spectrum (hexadeuterated dimethyl sulfoxide) δ ppm: 1.22 (3H, singlet); 1.50 (3H, singlet); 3.78 (1H, doublet, J=10 Hz); 4.16–5.26 (2H, multiplet); 7.20 (1H, doublet, J=8 Hz); 7.98 (1H, doublet of doublets, J=8 & 2 Hz); 8.62 (1H, doublet, J=2 Hz); 9.04 (3H, broad singlet).

Infrared Absorption Spectrum (KBr) $\nu_{max}$ cm$^{-1}$: 3330, 1360.

Mass spectrum (m/e): 326 (M++1).

Elemental analysis: Calculated for C$_{12}$H$_{15}$ClF$_3$NO$_4$S: C, 39.84%; H, 4.18%; N, 3.87%; Cl, 9.80%; F, 15.75%; S, 8.86%. Found: C, 40.05%; H, 4.41%; N, 3.89%; Cl, 9.98%; F, 15.76%; S, 8.79%.

PREPARATION 10

2,2-Dimethyl-6-pentafluoroethylthio-2H-1-benzopyran

A solution of 1.463 g of 6-mercapto-2,2-dimethyl-2H-1-benzopyran (prepared as described in Preparation 6) in 15 ml of dimethylformamide was added dropwise, whilst ice-cooling, to a suspension of 0.366 g of sodium hydride (as a 55% w/w dispersion in mineral oil) in 15 ml of dimethylformamide under an atmosphere of nitrogen. After the reaction mixture had been stirred for 15 minutes, 5.53 g of perfluoroethyl iodide were added to it. The reaction mixture was then stirred whilst ice-cooling for 1 hour and then at room temperature for 2 hours. At the end of this time, the reaction mixture was poured into 150 ml of dilute aqueous hydrochloric acid and extracted with ethyl acetate. The extract was washed with water, with an aqueous solution of sodium hydrogencarbonate and with a saturated aqueous solution of sodium chloride, in that order, after which it was dried over anhydrous sodium sulfate. The solvent was removed by distillation under reduced pressure, and the resulting residue was purified by column chromatography through silica gel, using a 20:1 by volume mixture of cyclohexane and ethyl acetate as the eluent, to afford 1.935 g of the title compound as an oil.

Nuclear Magnetic Resonance Spectrum (CDCl$_3$) δ ppm: 1.40 (6H, singlet); 5.64 (1H, doublet, J=10 Hz); 6.30 (1H, doublet, J=10 Hz); 6.78 (1H, doublet, J=8 Hz); 7.24 (1H, doublet, J=2 Hz); 7.38 (1H, doublet of doublets, J=8 & 2 Hz).

Mass spectrum (m/e): 310 (M+).

PREPARATION 11

3,4-Epoxy-3,4-dihydro-2,2-dimethyl 6-pentafluoroethylsulfonyl-2H-1-benzopyran Following a procedure similar to that described in Preparation 3, but using 1.87 g of 2,2-dimethyl-6-pentafluoroethylthio-2H-1-benzopyran (prepared as described in Preparation 10) and 5.35 g of 3-chloroperoxybenzoic acid, 1.70 g of the title compound was obtained as an oil.

Nuclear Magnetic Resonance Spectrum (CDCl$_3$) δ ppm: 1.34 (3H, singlet); 1.62 (3H, singlet); 3.56 (1H, doublet, J=4 Hz); 4.00 (1H, doublet, J=4 Hz); 7.02 (1H, doublet, J=8 Hz); 8.92 (1H, doublet of doublets, J=8 & 2 Hz); 9.06 (1H, doublet, J=2 Hz).

Mass spectrum (m/e): 358 (M+).

PREPARATION 12 trans-4-Amino-3,4-dihydro-2,2-dimethyl-6-pentafluoroethyl-2H-1-benzopyran-3-ol hydrochloride Following a procedure similar to that described in Preparation 4, but using 0.247 g of 3,4-epoxy-3,4-dihydro-2,2-dimethyl-6-pentafluoroethylsulfonyl-2H-1-benzopyran-3-ol (prepared as described in Preparation 11) and aqueous ammonia, 0.245 g of the title compound were obtained as crystals.

Melting point: 250°–252° C.

Nuclear Magnetic Resonance Spectrum (hexadeuterated dimethyl sulfoxide) δ ppm: 1.28 (3H, singlet); 1.48 (3H, singlet); 3.62–3.92 (1H, multiplet); 4.36 (1H, doublet, J=10 Hz); 6.46–6.70 (1H, multiplet); 7.20 (1H, doublet, J=8 Hz); 7.94 (1H, doublet of doublets, J=8 & 2 Hz); 8.58 (1H, doublet, J=2 Hz); 8.98 (3H, broad singlet).

Infrared Absorption Spectrum (KBr) $\nu_{max}$ cm$^{-1}$: 3230, 3020, 2940, 1220, 1120.

Mass spectrum (m/e): 374 (M++1).

PREPARATION 13 trans-3,4-Dihydro 2,2-dimethyl-4-(1-oxoisoindolin-2-yl)-6-trifluoromethylsulfonyl-2H-1-benzopyran-3-ol

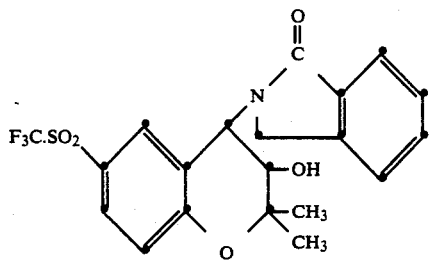

A solution of 0.18 g of zinc chloride and 0.083 g of sodium cyanoborohydride in 3 ml of methanol was added to a solution of 0.40 g of trans-4-amino-3,4-dihydro-2,2-dimethyl-6-trifluoromethylsulfonyl-2H-1-benzopyran-3-ol (prepared from its hydrochloride prepared as described in Preparation 9) and 0.20 g of methyl 2-formylbenzoate in 6 ml of methanol, and the resulting mixture was stirred at room temperature for 1 hour and then at 50° C. for 24 hours. At the end of this time, the mixture was cooled with ice and then mixed with a saturated aqueous solution of sodium hydrogencarbonate. The methanol was then removed by distillation under reduced pressure, and the resulting residue was diluted with water and extracted with methylene chloride. The extract was washed with water and with a saturated aqueous solution of sodium chloride, in that order, and dried over anhydrous magnesium sulfate; the solvent was then removed by distillation under reduced pressure. The resulting residue was recrystallized from ethyl acetate, to afford 0.34 g of the title compound, melting at 279°–281° C.

Nuclear Magnetic Resonance Spectrum (hexadeuterated dimethyl sulfoxide) δ ppm: 1.35 (3H, singlet); 1.56 (3H, singlet); 3.98 (1H, doublet of doublets, J=6 & 11 Hz); 4.08 (1H, doublet, J=17 Hz); 4.60 (1H, doublet, J=17 Hz); 5.43 (1H, doublet, J=11 Hz); 5.89 (1H, doublet, J=6 Hz); 7.17 (1H, doublet, J=9 Hz); 7.4–8.1 (6H, multiplet).

Infrared Absorption Spectrum (KBr) $\nu_{max}$ cm$^{-1}$: 3473, 1671.

Mass spectrum (m/e): 441 (M+).

Elemental analysis: Calculated for $C_{20}H_{18}F_3NO_5S$: C, 54.42%; H, 4.11%; N, 3.17%. Found: C, 54.50%; H, 4.31%; N, 2.88%.

We claim:

1. A compound of formula (I):

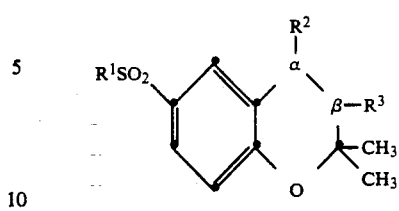

in which:

$R^1$ represents a trifluoromethyl group or a pentafluoroethyl group;

$R^2$ represents a group of formula (II):

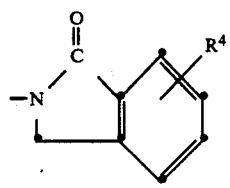

in which $R^4$ represents a hydrogen atom;

α-β represents a carbon-carbon single bond; and $R^3$ represents a nitrooxy group;

or a pharmaceutically acceptable salt thereof.

2. The compound of claim 1, wherein $R^1$ is a pentafluoroethyl group.

3. The compound of claim 1, which is 3,4-dihydro-2,2-dimethyl-4-(1-oxoisoindolin-2-yl)-6-trifluoromethylsulfonyl-2H-1-benzopyran-3-yl nitrate.

4. A composition for the treatment of cardiovascular disease, which comprises an effective amount of an active compound in admixture with a carrier or diluent, wherein the active compound is a compound of formula (I) or a pharmaceutically acceptable salt thereof, as claimed in claim 1.

5. The composition of claim 4, wherein $R^1$ is a trifluoromethyl group.

6. The composition of claim 4, wherein $R^1$ is a pentafluoroethyl group.

7. A method of treatment hypertension, congestive heart failure and angina pectoris which comprises administering to an animal an effective amount of an active compound, wherein the active compound is a compound of formula (I) or a pharmaceutically acceptable salt thereof, as claimed in claim 1.

8. The method of claim 7, wherein $R^1$ is a trifluoromethyl group.

9. The method of claim 7, wherein $R^1$ is a pentafluoroethyl group.

* * * * *